United States Patent [19]

Kellogg

[11] 4,287,181

[45] Sep. 1, 1981

[54] DERIVATIVES OF 6β-HYDROXYALKYLPENICILLANIC ACIDS AS β-LACTAMASE INHIBITORS

[75] Inventor: Michael S. Kellogg, Waterford, Conn.

[73] Assignee: Pfizer Inc., New York, N.Y.

[21] Appl. No.: 86,864

[22] Filed: Oct. 22, 1979

[51] Int. Cl.³ .......................................... C07D 499/00
[52] U.S. Cl. .................................. 424/114; 424/271; 260/245.2 R; 424/246
[58] Field of Search .............................. 424/271, 114; 260/245.2, 239.1

[56] References Cited

U.S. PATENT DOCUMENTS

| | | | |
|---|---|---|---|
| 4,053,468 | 10/1977 | Holden | 260/245.2 |
| 4,093,625 | 6/1978 | Commons et al. | 260/245.2 |
| 4,123,539 | 10/1978 | DiNinno | 424/270 |
| 4,143,046 | 3/1979 | Sheehan et al. | 260/306.7 |

OTHER PUBLICATIONS

DiNinno et al., J. Org. Chem., vol. 42, 2960, (1977).
Sheehan et al., J. Org. Chem., vol. 39, 1444, (1974).
Roets et al., J. Org. Chem. Soc., Perkin I, 704, (1976).

*Primary Examiner*—Nicholas S. Rizzo
*Attorney, Agent, or Firm*—Charles J. Knuth; Peter C. Richardson; James M. McManus

[57] ABSTRACT

6β-Hydroxyalkylpenicillanic acids and derivatives thereof as useful enhancers of the effectiveness of several β-lactam antibiotics against many β-lactamase producing bacteria, and 6β-substituted penicillanic acid benzyl ester derivatives as useful intermediates leading to said agents which enhance the effectiveness of β-lactam antibiotics.

37 Claims, No Drawings

DERIVATIVES OF 6β-HYDROXYALKYLPENICILLANIC ACIDS AS β-LACTAMASE INHIBITORS

BACKGROUND OF THE INVENTION

One of the most well-known and widely used class of antibacterial agents are the so-called β-lactam antibiotics. These compounds are characterized in that they have a nucleus consisting of a 2-azetidinone (β-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the β-lactam antibiotics as valuable chemotherapeutic agents, they suffer from the major drawback that certain members are not active against certain microorganisms. It is thought that in many instances this resistance of a particular microorganism to a given β-lactam antibiotic results because the microorganism produces a β-lactamase. The latter substances are enzymes which cleave the β-lactam ring of penicillins and cephalosporins to give products which are devoid of antibacterial activity. However, certain substances have the ability to inhibit β-lactamases, and when a β-lactamase inhibitor is used in combination with a penicillin or cephalosporin it can increase or enhance the antibacterial effectiveness of the penicillin or cephalosporin against certain β-lactamase producing microorganisms. It is considered that there is an enhancement of antibacterial effectiveness when the antibacterial activity of a combination of a β-lactamase inhibiting substance and a β-lactam antibiotic is significantly greater than the sum of the antibacterial activities of the individual components against β-lactamase producing microorganisms.

The present invention relates to a series of 6β-hydroxyalkylpenicillanic acids and esters thereof readily hydrolyzable in vivo which are potent inhibitors of microbial β-lactamases and which enhance the effectiveness of β-lactam antibiotics. The invention further relates to benzyl 6β-hydroxyalkylpenicillanates, said esters being useful chemical intermediates to the corresponding acids.

Pharmaceutical compositions comprising the abovementioned 6β-substituted penicillanic acids and readily hydrolyzable esters thereof with certain β-lactam antibiotics as well as a method for increasing the effectiveness of certain β-lactam antibiotics in combination with the above-mentioned 6β-substituted penicillanic acids and readily hydrolyzable esters thereof are also parts of the present invention.

Di Ninno, et. al., [J. Org. Chem., 42, 2960 (1977)] have reported the synthesis of 6β-hydroxyalkylpenicillanic acids and the corresponding benzyl esters as potential antibacterial agents and useful intermediates, respectively.

6-Ethylpenicillanic acid and its sulfoxide derivative are claimed as antibiotics in U.S. Pat. No. 4,123,539.

6α-Hydroxypenicillanic acid and esters thereof have been prepared from 6-diazopenicillanic acid and the corresponding esters [J. Org. Chem., 39 1444 (1974)].

U.S. Pat. No. 4,143,046 discloses 6β-substituted sulfonyloxypenicillanic acids as antibacterial agents.

SUMMARY OF THE INVENTION

The compounds of this invention are of the formulae

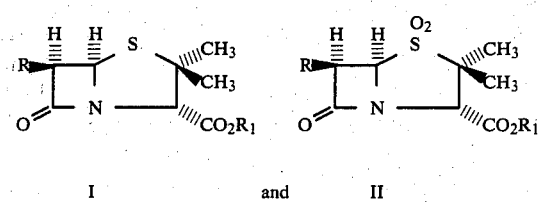

I and II or a pharmaceutically acceptable base salt thereof, wherein R is alkylsulfonyloxymethyl having one to four carbon atoms in the alkyl group, phenylsulfonyloxymethyl, substituted phenylsulfonyloxymethyl wherein said substituent is methyl, methoxy, fluoro, chloro, bromo or trifluoromethyl or 1-hydroxy-3-phenylpropyl; $R_1$ is benzyl, hydrogen or ester-forming residues readily hydrolyzable in vivo; and $R_2$ is

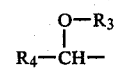

wherein $R_3$ is sulfo, hydrogen, alkoxycarbonyl of two to four carbon atoms, alkanoyl of two to eighteen carbon atoms, benzoyl, substituted benzoyl wherein said substituent is amino, methyl, methoxy, fluoro, chloro, bromo or trifluoromethyl, alkylsulfonyl of one to four carbon atoms, phenylsulfonyl or substituted phenylsulfonyl wherein said substituent is methyl, methoxy, fluoro, chloro, bromo or trifluoromethyl; and $R_4$ is hydrogen, alkyl of one to four carbon atoms, phenyl, benzyl, pyridyl or β-phenethyl.

A preferred group of β-lactamase inhibitors are those of formula II wherein $R_1$ and $R_4$ are each hydrogen. Especially preferred within this group are those compounds wherein $R_3$ is hydrogen, acetyl, stearoyl or benzoyl.

A second group of preferred compounds related to II are those wherein $R_1$ and $R_3$ are each hydrogen and $R_4$ is alkyl of one to four carbon atoms. Especially preferred within this group are the compounds wherein $R_4$ is methyl.

A third group of preferred compounds of formula I are those wherein $R_1$ is hydrogen. Especially preferred within this group are those compounds wherein R is methylsulfonyloxymethyl, p-toluenesulfonyloxymethyl and 1-hydroxy-3-phenylpropyl.

The present invention also relates to a pharmaceutical composition useful for treating bacterial infections in mammals, which comprises a pharmaceutically acceptable carrier, a β-lactam antibiotic and a compound selected from the formulae

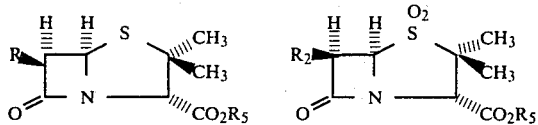

III and IV or a pharmaceutically acceptable base salt thereof, wherein R is alkylsulfonyloxymethyl having one to four carbon atoms in the alkyl group, phenylsulfonyloxymethyl, substituted phenylsulfonyloxymethyl wherein said substituent is methyl, methoxy, fluoro, chloro, bromo or trifluoromethyl or 1-hydroxy-3-phenylpropyl; $R_2$ is

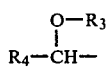

wherein $R_3$ is sulfo, hydrogen, alkoxycarbonyl of two to four carbon atoms, alkanoyl of two to eighteen carbon atoms, benzoyl, substituted benzoyl wherein said substituent is amino, methyl, methoxy, fluoro, chloro, bromo or trifluoromethyl, alkylsulfonyl of one to four carbon atoms, phenylsulfonyl or substituted phenylsulfonyl wherein said substitutent is methyl, methoxy, fluoro, chloro, bromo or trifluoromethyl; $R_4$ is hydrogen, alkyl of one to four carbon atoms, phenyl, pyridyl, benzyl or β-phenethyl; and $R_5$ is hydrogen or ester-forming residue readily hydrolyzable in vivo.

Preferred compounds are those of formulae III and IV wherein $R_5$ is hydrogen or ester-forming residues readily hydrolyzable in vivo selected from alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, and γ-butyrolacton-4-yl, and said β-lactam antibiotics are selected from penicillins and cephalosporins. Especially preferred are compounds of formula IV wherein $R_4$ and $R_5$ are each hydrogen and $R_3$ is hydrogen, acetyl, stearoyl or benzoyl. Also especially preferred is the compound wherein $R_3$ and $R_5$ are each hydrogen and $R_4$ is methyl. Especially preferred are compounds of formula III wherein R is methylsulfonyloxymethyl, p-toluenesulfonyloxymethyl and 1-hydroxy-3-phenylpropyl.

The invention also consists of a method for increasing the effectiveness of a β-lactam antibiotic in a mammalian subject which comprises co-administration to said subject a β-lactam antibiotic effectiveness increasing amount of a compound of the formulae

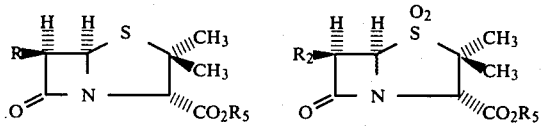

III IV or a pharmaceutically acceptable base salt thereof wherein R is alkylsulfonyloxymethyl having one to four carbon atoms in the alkyl group, phenylsulfonyloxymethyl, substituted phenylsulfonyloxymethyl wherein said substituent is methyl, methoxy, fluoro, chloro, bromo or trifluoromethyl or 1-hydroxy-3-phenylpropyl; $R_2$ is

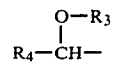

wherein $R_3$ is sulfo, hydrogen, alkoxycarbonyl of two to four carbon atoms, alkanoyl of two to eighteen carbon atoms, benzoyl, substituted benzoyl wherein said substituent is amino, methyl, methoxy, fluoro, chloro, bromo or trifluoromethyl, alkylsulfonyl of one to four carbon atoms, phenylsulfonyl or substituted phenylsulfonyl wherein said substituent is methyl, methoxy, fluoro, chloro, bromo or trifluoromethyl and $R_4$ is hydrogen, alkyl of one to four carbon atoms, phenyl, benzyl, pyridyl or β-phenethyl; and $R_5$ is hydrogen or ester-forming residue readily hydrolyzable in vivo.

Preferred compounds are those of formula III and IV wherein $R_5$ is hydrogen or ester-forming residues readily hydrolyzable in vivo selected from alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and γ-butyrolacton-4-yl, and said β-lactam antibiotics are selected from penicillins and cephalosporins. Especially preferred are compounds related to IV wherein $R_4$ and $R_5$ are each hydrogen and $R_3$ is hydrogen, acetyl, stearoyl or benzoyl. Also especially preferred of this class is the compound wherein $R_3$ and $R_5$ are each hydrogen and $R_4$ is methyl.

Especially preferred are compounds of formula III wherein R is methylsulfonyloxymethyl, p-toluenesulfonyloxymethyl and 1-hydroxy-3-phenylpropyl.

The definition of the aforementioned ester-forming residues is meant to embrace any ester which is readily hydrolyzed in a mammal. Especially preferred are ester-forming residues readily hydrolyzable in vivo selected from alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, and γ-butyrolacton-4-yl.

The preferred β-lactams whose antibiotic activity is enhanced by the 6β-hydroxyalkylpenicillanic acid sulfones of the present invention are selected from:
  6-(2-phenylacetamido)penicillanic acid,
  6-(2-phenoxyacetamido)penicillanic acid,
  6-(2-phenylpropionamido)penicillanic acid,
  6-(D-2-amino-2-phenylacetamido)penicillanic acid,
  6-(D-2-amino-2-[4-hydroxyphenyl]acetamido)penicillanic acid,
  6-(D-2-amino-2-[1,4-cyclohexadienyl]acetamido)penicillanic acid,
  6-(1-aminocyclohexanecarboxamido)penicillanic acid, 6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)-penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-2-[3-methylsulfonylimidazolidin-2-one-1-carboxamido]-2-phenylacetamido)penicillanic acid,
6-([hexahydro-1H-azepin-1-yl]methyleneamino)-penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)-penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)-penicillanic acid,
6-(2-tolyloxycarbonyl-2-[3-thienyl]acetamido)-penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)-penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-formyloxy-2-phenylacetamido)-3-(5-[1-methyltetrazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(D-2-amino-2-p-hydroxypehnylacetamido)-desacetoxycephalosporanic acid,
7-(2-[4-pyridylthio]acetamido)cephalosporanic acid,
7-(D-2-amino-2[1,4-cyclohexadienyl]acetamido)-cephalosporanic acid,
7-(D-2-amino-2-phenylacetamido)cephalosporanic acid,
7-[D-(-)-alpha-(4-ethyl-2,3-dioxo-1-piperazinecarboxamido)-alpha-(4-hydroxyphenyl)acetamido]-3-[(1-methyl-1,2-3,4-tetrazol-5-yl)thiomethyl]-3-cephem-4-carboxylic acid,
7-(D-2-amino-2-phenylacetamido)-3-chloro-3-cephem-4-carboxylic acid,
7-[2-(2-amino-4-thiazolyl)-2-(methoximino)acetamido]cephalosporanic acid,
[6R, 7R-3-carbamoyloxymethyl-7(2Z)-2-methoxyimino(fur-2-yl)acetamido-ceph-3-em-4-carboxylate]
7-[2-(2-aminothiazol-4-yl)acetamido]-3-[((1-2-dimethylaminoethyl)-1H-tetrazol-5-yl]thio)methyl]-ceph-3-em-4-carboxylic acid, and a pharmaceutically acceptable salts thereof.

Detailed Description of the Invention

The β-lactamase inhibitors of the present invention are conveniently prepared starting with benzyl 6,6-dibromopenicillanate. The condensation of an appropriate aldehyde with the enolate formed through the reaction of benzyl 6,6-dibromopenicillanate with an organometallic reagent, such as the process taught by Di Ninno, et. al., J. Org. Chem., 42, 2960 (1977), results in the formation of a benzyl 6-bromo-6-hydroxyalkyl-penicillanate, the initial intermediate leading to the products of the present invention.

The product of this initial condensation is comprised of diastereomeric mixtures due to two asymmetric centers, one at the 6-position of the penam nucleus and the second at the carbon atom in the chain at the 6-position, shown as follows:

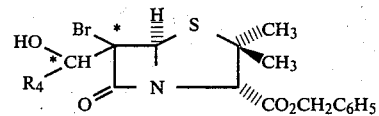

As one skilled in the art can readily determine, of these only one is an asymmetric center in this intermediate product when $R_4$ is hydrogen.

The substituents at the 6-position are designated as α or β and are so indicated in the structural formula by a broken or solid bond, respectively. The stereochemical configuration of the substituent in the side chain is designated as (R) or (S) (Cahn, et. al., Experientia, 12, 81 (1956). The assignment of configuration is based on nuclear-magnetic-resonance spectroscopy.

Experimentally, benzyl 6,6-dibromopenicillanate in a reaction-inert solvent at −20° to −78° C. is treated with about one equivalent of t-butyl lithium or t-butyl magnesium chloride. The resulting enolate is then treated with the appropriate aldehyde and, after a short reaction period, the reaction is quenched and the product isolated by conventional means.

The addition of zinc chloride to a solution of the enolate prior to the addition of aldehyde appears to exert control over the stereochemistry of the condensation product. Accordingly, a high preponderance of (S)

configuration in the side chain is obtained under these conditions.

When diethyl zinc is employed as the initial organometallic reagent a preponderance of (R) configuration in the side chain of the product is obtained.

The initial reaction is conducted in an anhydrous reaction-inert solvent, which appreciably solubilizes the reactants without reacting to any great extent with the reactants or products under reaction conditions. It is preferred that said solvents have boiling points and freezing points compatible with reaction temperatures. Such solvents or mixtures thereof include aromatic solvents such as toluene and ethereal solvents such as tetrahydrofuran and diethyl ether.

The molar ratio of the starting penicillanate derivative and the organometallic reagent is not critical to the process. The use of a slight excess of organometallic, up to as much as a ten percent above an equimolar quantity, aids in the completion of the reaction and offers no serious problems in isolating the desired product in purified form.

Moisture can effectively be kept out of the reaction by employing a nitrogen or argon atmosphere.

Reaction time is inherently dependent on concentration, reaction temperature and reactivity of the starting reagents. When the reaction is conducted at the preferred reaction temperature of −60° to −78° C. the reaction time for the formation of the enolate is about 30–45 minutes. The reaction time for the formation of the intermediate product from the aforementioned enolate and aldehyde is about 30–60 minutes.

On completion of the reaction, the product is isolated by conventional means and the diastereomeric mixture can be separated by column chromatography. However, the nature of the next reaction, which is the removal of the 6-bromo substituent, precludes the necessity for said separation of α and β epimers at C-6.

Treatment of the benzyl 6-bromo-6-hydroxyalkylpenicillanate, resulting from the first reaction, with tri-n-butyltin hydride leads to the formation of a benzyl 6-hydroxyalkylpenicillanate in which the 6-hydroxyalkyl moiety is in the β-configuration. This result is independent of the conformation of the substituents at the 6-position of the starting reagents. Thus 6α-bromo-6β-hydroxyalkyl esters and 6β-bromo-6α-hydroxyalkyl esters both give, on treatment with tri-n-butyltin hydride, the same 6β-hydroxyalkyl ester as the main product, assuming all other structural parameters in the compounds are the same.

The reaction is carried out in a reaction-inert solvent which appreciably solubilizes the reactants without reacting to any great extent with the reactants or the product under reaction conditions. It is further preferred that said solvent be an aprotic solvent, immiscible with water and have a boiling and freezing point compatible with reaction temperatures. Such solvents or mixtures thereof include the preferred solvents benzene and toluene.

Reaction time is dependent on concentration, reaction temperature and reactivity of the reagents. When the reaction is carried out at the preferred temperature, the reflux temperature of the solvent, the reaction is usually complete in about 4–5 hours.

The molar ratio of the reagents is not critical to the process. Usually an excess of the tin hydride is employed and as much as a 100% excess over an equimolar amount can be employed.

When the reaction is complete the solvent is removed and the residue triturated with hexane to remove the organotin by-product. The intermediate product can be purified and the isomers separated by column chromatography.

The oxidation of the resulting benzyl 6β-(S) and (R)hydroxyalkylpenicillanate to the corresponding sulfones of formula II wherein $R_1$ is benzyl is conveniently carried out using an organic peroxy acid, e.g., a peroxycarboxylic acid such as m-chloroperbenzoic acid. The reaction is carried out by reacting the appropriate benzyl 6β-(R) or (S)hydroxyalkylpenicillanate with about 2 to about 4 equivalents and preferably about 2.2 equivalents of the oxidant in a reaction-inert solvent. Typical solvents are chlorinated hydrocarbons, such as methylene chloride, chloroform and 1,2-dichloroethane.

The oxidant and substrate are initially combined in a solvent at 0°–5° C. The temperature is allowed to rise to room temperature. Reaction time is about 3–6 hours.

During isolation of the sulfones, which are useful intermediates, the solvent is removed and the residue partitioned between water and a water immiscible solvent such as ethyl acetate. The pH of the water-organic solvent mixture is adjusted to 7.0 and any excess peroxide is decomposed with sodium bisulfite. The intermediate product, which is contained in the organic phase, is isolated and purified by conventional means.

The biologically active products of the present invention of formula I and II wherein $R_1$ is hydrogen are prepared by debenzylation of the corresponding benzyl esters. Accordingly, the appropriate benzyl ester is added to a suspension of prehydrogenated 5% palladium-on-calcium carbonate catalyst in a 50% methanol-water solution. The hydrogenolysis is conducted at room temperature and is usually conducted at 45–50 psi pressure. Under these conditions the reaction is usually complete in 30–60 minutes. Filtration of the spent catalyst followed by removal of the solvent by freeze drying results in the isolation of the calcium salt. Acidification of the filtrate, after removal of the catalyst, followed by extraction with a water immiscible solvent such as ethyl acetate, results in isolation of the free acid wherein $R_1$ is hydrogen.

Alternatively, the compounds of formula II wherein $R_1$ is hydrogen can also be prepared by the same series of reactions previously described, but in a different sequential order. For example, the initially formed benzyl 6-bromo-6-hydroxyalkylpenicillanates can be oxidized as previously described followed by removal of the 6-bromo substituent with tri-n-butyltin hydride and debenzylation.

Compounds of the present invention of formula II wherein $R_3$ is alkanoyl are prepared by acylation of the requisite benzyl 6β-hydroxyalkylpenicillanate sulfone followed by hydrogenolysis of the benzyl ester to give those compounds of formula II wherein $R_3$ is as indicated and $R_1$ is hydrogen.

The acylation is carried out by contacting the appropriate penicillanate sulfone with an equimolar amount of the requisite acid halide, plus as much as a 10–20% excess, in a reaction-inert solvent such as methylene chloride. A tertiary amine, added in molar amounts corresponding to the acid halide, acts as a scavenger for the hydrogen halide formed.

The acylation is conducted at a reaction temperature of about 0°–5° C. and requires a reaction time of about 20–30 minutes. The intermediate product is obtained by removing the solvent and treating the resulting residue with water-ethyl acetate and the organic phase is evaporated to give the desired materials.

The formation of the final products, compounds of formula II wherein $R_3$ is alkanoyl and $R_1$ is hydrogen, is carried out by debenzylation under conditions hereinbefore described.

The compounds of the present invention of formula II wherein $R_3$ is benzoyl, said substituted benzoyl, or said alkoxycarbonyl are all prepared in a manner similar to the preparation of those compounds wherein $R_3$ is alkanoyl, and comprises initial acylation of the appropriate benzyl 6$\beta$-hydroxyalkylpenicillanate sulfone followed by removal of the benzyl moiety from ester.

The compounds of the present invention of formula I wherein R is said alkylsulfonyloxymethyl, phenylsulfonyloxymethyl or said substituted phenylsulfonyloxymethyl and of formula II wherein $R_3$ is said alkylsulfonyl, phenylsulfonyl or said substituted phenylsulfonyl are most conveniently prepared by the initial acylation of the requisite benzyl 6$\beta$-hydroxyalkylpenicillanate with about an equimolar amount of the appropriate sulfonyl chloride, employing pyridine as the solvent and at a reaction temperature of 0° C. and reaction time of about 2–3 hours. The product is isolated by quenching of the reaction mixture with water followed by extraction and purification.

The second reaction in the series comprises debenzylation of the intermediate ester using hydrogen and 5% palladium-on-calcium carbonate, a procedure previously described.

The final step to compounds of formula II comprises oxidation of the 6$\beta$-sulfonyloxyalkylpenicillanic acids with potassium permanganate in a mixture of water-methylene chloride at ambient temperatures at a pH of 6–6.4. Following the reaction, which requires about 45–60 minutes, the pH is adjusted to 1.5 and the product isolated from the organic phase.

The synthesis of those compounds of formula II wherein $R_3$ is sulfo is effected by the reaction of the appropriate benzyl 6$\beta$-hydroxyalkylpenicillanate sulfone with sulfur trioxide-pyridine complex in dimethylformamide at room temperature for 45–60 minutes.

The product, which is isolated as the pyridinium salt, is debenzylated with hydrogen and 5% palladium-on-calcium carbonate, as previously described.

When $R_1$ is an ester-forming residue readily hydrolyzable in vivo in a compound of formula I or II it is a group which is notionally derived from an alcohol of the formula $R_1$-OH, such that the moiety $COOR_1$ in such a compound of formula I or II represents an ester grouping. Moreover, $R_1$ is of such a nature that the grouping $COOR_1$ is readily cleaved in vivo to liberate a free carboxy group (COOH). That is to say, $R_1$ is a group of the type that when a compound of formula I or II, wherein $R_1$ is an ester-forming residue readily hydrolyzed in vivo, is exposed to mammalian blood or tissue, the compound of formula I or II, wherein $R_1$ is hydrogen, is readily produced. The groups $R_1$ are known in the penicillin art. In most instances they improve the absorption characteristics of the penicillin compound. Additionally, $R_1$ should be of such a nature that it imparts pharmaceutically-acceptable properties to a compound of formula I or II, and it liberates pharmaceutically-acceptable fragments when cleaved in vivo.

As indicated above, the groups $R_1$ are known and are readily identified by those skilled in the penicillin art, as taught in West German application 2,517,316. Typical groups for $R_1$ are 3-phthalidyl, 4-crotonolactonyl, $\gamma$-butyrolacton-4-yl, alkanoyloxyalkyl and alkoxycarbonyloxyalkyl. However, preferred groups for $R_1$ are alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and $\gamma$-butyrolacton-4-yl.

Compounds of the formula I or II, wherein $R_1$ is an ester-forming residue readily hydrolyzable in vivo, can be prepared directly from the compound of formula I or II, wherein $R_1$ is hydrogen, by esterification. The specific method chosen will depend naturally upon the precise structure of the ester-forming residue, but an appropriate method will be readily selected by one skilled in the art. In the case wherein $R_1$ is selected from the group consisting of 3-phthalidyl, 4-crotonolactonyl, $\gamma$-butyrolacton-4-yl, alkanoyloxyalkyl and alkoxycarbonyloxyalkyl they can be prepared by alkylation of the compound of formula I or II, wherein $R_1$ is hydrogen, with a 3-phthalidyl halide, a 4-crotonolactonyl halide, a $\gamma$-butyrolacton-4-yl halide, an alkanoyloxyalkyl halide or an alkoxycarbonyloxyalkyl halide. The term "halide" is intended to mean derivatives of chlorine, bromine and iodine. The reaction is conveniently carried out by dissolving a salt of the compound of formula I or II, wherein $R_1$ is hydrogen, in a suitable polar organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salt, and tertiary amine salts, such as triethylamine, N-ethylpiperidine, N,N-dimethylaniline and N-methylmorpholine salts. The reaction is run at a temperature in the range from about 0° to 50° C., and usually at about 0°–25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from 1 to about 24 hours are commonly used.

The compounds of formula I and II, wherein $R_1$ is hydrogen, are acidic and will form salts with basic agents. Such salts are considered to be within the scope of this invention. These salts can be prepared by standard techniques, such as contacting the acidic and basic components, usually in a 1:1 molar ratio, in an aqueous, nonaqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of formula I and II wherein $R_1$ is hydrogen are the sodium, potassium and triethylamine salts.

As indicated hereinbefore, the compounds of the formula I and II, wherein $R_1$ is hydrogen or an ester-forming residue readily hydrolyzable in vivo, are potent inhibitors of microbial β-lactamases, and they increase the antibacterial effectiveness of β-lactam antibiotics (penicillins and cephalosporins) against many microorganisms, particularly those which produce a β-lactamase. The ability of the said compounds of the formula I or II increase the effectiveness of a β-lactam antibiotic can be appreciated by reference to experiments in which the MIC of a given antibiotic alone, and a compound of the formula I or II alone, are measured. These MIC's are then compared with the MIC values obtained with a combination of the given antibiotic and the compound of the formula I or II. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology," edited by Lenette, Spaulding and Truant, 2nd edition, 1974, American Society for Microbiology.

The compounds of the formula I and II, wherein $R_1$ is hydrogen or an ester-forming residue readily hydrolyzable in vivo, enhance the antibacterial effectiveness of β-lactam antibiotics in vivo. That is, they lower the amount of the antibiotic which is needed to protect mice against an otherwise lethal inoculum of certain β-lactamase producing bacteria.

The ability of the compounds of formula I and II, wherein $R_1$ is hydrogen or an ester-forming residue readily hydrolyzable in vivo, to enhance the effectiveness of a β-lactam antibiotic against β-lactamase-producing bacteria makes them valuable for co-administration with β-lactam antibiotics in the treatment of bacterial infections in mammals, particularly man. In the treatment of a bacterial infection, the said compound of the formula I or II can be comingled with the β-lactam antibiotic, and the two agents thereby administered simultaneously. Alternatively, the said compound of the formula I or II can be administered as a separate agent during a course of treatment with a β-lactam antibiotic. In some instances it will be advantageous to pre-dose the subject with the compound of the formula I or II before initiating treatment with a β-lactam antibiotic.

When using a compound of formula I or II wherein $R_1$ is hydrogen or an ester group readily hydrolyzable in vivo to enhance the effectiveness of β-lactam antibiotic, a mixture of I or II with the β-lactam antibiotic is administered preferably in formulation with standard pharmaceutical carriers or diluents. A pharmaceutical composition comprising a pharmaceutically-acceptable carrier, a β-lactam antibiotic and a compound of formula I or II wherein $R_1$ is hydrogen or a readily hydrolyzable ester thereof will normally contain from about 5 to about 80 percent of the pharmaceutically acceptable carrier by weight.

When using the compounds of formula I or II wherein $R_1$ is hydrogen or an ester group readily hydrolyzable in vivo in combination with another β-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula I or II and the β-lactam antibiotic will normally be in the range from about 1:3 to 3:1. Additionally, when using the compounds of formula I or II in combination with another β-lactam antibiotic, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some case it may be necessary to use dosages outside these limits.

Typical β-lactam antibiotics with which the compounds of formula I or II and its esters readily hydrolyzable in vivo can be co-administered are:

6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)-penicillanic acid,
6-(D-2-amino-2-[1,4-cyclohexadienyl]acetamido)-penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)-penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-2-[3-methylsulfonylimidazolidin-2-one-1-carboxamido]-2-phenylacetamido)penicillanic acid,
6-([hexahydro-1H-azepin-1-yl]methyleneamino)-penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate, pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)-penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)-penicillanic acid,
6-(2-tolyloxycarbonyl-2-[3-thienyl]acetamido)-penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-formyloxy-2-phenylacetamido)-3-(5-[1-methyltetrazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(D-2-amino-2-p-hydroxypehnylacetamido)-desacetoxycephalosporanic acid,
7-(2-[4-pyridylthio]acetamido)cephalosporanic acid,
7-(D-2-amino-2[1,4-cyclohexadienyl]acetamido)-cephalosporanic acid,
7-(D-amino-2-phenylacetamido)cephalosphoranic acid,
7-[D-(-)-alpha-(4-ethyl-2,3-dioxo-1-piperazinecarboxamido)-alpha-(4-hydroxyphenyl)acetamido]-3-[(1-methyl-1,2-3,4-tetrazol-5-yl)thiomethyl]-3-cephem-4-carboxylic acid,
7-(D-2-amino-2-phenylacetamido)-3-chloro-3-cephem-4-carboxylic acid,
7-[2-(2-amino-4-thiazolyl)-2-(methoximino)acetamido]cephalosporanic acid,
[6R,7R-3-carbamoyloxymethyl-7(2Z)-2-methoxyimino(fur-2-yl)acetamido-ceph-3-em-4-carboxylate]
7-[2-(2-aminothiazol-4-yl)acetamido]-3-[([1-2-dimethylaminoethyl)-1H-tetrazol-5-yl]thio)methyl]-ceph-3-em-4-carboxylic acid, and a pharmaceutically acceptable salts thereof.

As will be appreciated by one skilled in the art, some of the above β-lactam compounds are effective when administered orally or parenterally, while others are effective only when administered by the parenteral route. When compounds of formula I wherein $R_1$ is hydrogen or an ester group readily hydrolyzable in vivo is to be used simultaneously (i.e. co-mingled) with a β-lactam antibiotic which is effective only on parenteral administration, a combination formulation suitable for parenteral use will be required. When the compounds of formula I wherein $R_1$ is hydrogen or an ester group is to be used simultaneously (co-mingled) with a β-lactam antibiotic which is effective orally or parenterally, combinations suitable for either oral or parenteral administration can be prepared. Additionally, it is possible to administer preparations of the compounds of formula I orally, while at the same time administering a further β-lactam antibiotic parenterally; and it is also possible to administer preparations of the compounds of formula I parenterally, while at the same time administering the further β-lactam antibiotic orally.

The following examples are provided solely for the purpose of further illustration. Nuclear magnetic resonance spectra (NMR) were measured at 60 MHz for solutions of deuterochloroform (CDCl$_3$), perdeutero dimethyl sulfoxide (DMSO-d$_6$) or deuterium oxide (D$_2$O) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet, t, triplet; q, quartet; m, multiplet.

EXAMPLE 1

6β-Hydroxymethylpenicillanic Acid Sulfone

A. benzyl 6-bromo-6-hydroxymethylpenicillanate

A solution of 44.9 g. of benzyl 6,6-dibromopenicillanate in 600 ml. of dry tetrahydrofuran was cooled to −78° C. and 56.4 ml. of t-butylmagnesium chloride was added dropwise with vigorous stirring under an inert atmosphere while maintaining the temperature at −60° C. After stirring 30 min. at −78° C. the solution was treated with gaseous formaldehyde in a stream of nitrogen until five molar equivalents had been added. The reaction was quenched at −78° C. by the addition of 5.7 ml. of acetic acid dropwise over a period of 25 min. The reaction solution was allowed to warm to room temperature and was concentrated in vacuo. To the residue was added 200 ml. of water and 200 ml. of ethyl acetate. The organic layer was separated and the water layer extracted again with ethyl acetate. The organic phases were combined, washed successively with water (200 ml.), 5% aqueous sodium bicarbonate (200 ml.) and brine (200 ml.) and dried over magnesium sulfate. Removal of the solvent under reduced pressure provides 38.2 g. of the desired product, epimeric at C-6.

B. benzyl 6β-hydroxymethylpenicillanate

A solution containing 10 g. of benzyl 6-bromo-6-hydroxymethylpenicillanate, 6.9 ml. tri-n-butyltin hydride and a trace of azobisisobutyronitrile in 200 ml. of benzene was refluxed for 5 hrs. under nitrogen. The reaction mixture was cooled and concentrated in vacuo. The residue was triturated with hexane and was chromatographed on silica gel, using toluene/ethyl acetate (2:1) as the eluent to give 7.5 g. of the product.

C. benzyl 6β-hydroxymethylpenicillanate sulfone m-Chloroperbenzoic acid (11.8 g.) was added to a solution of 7.5 g. of benzyl 6β-hydroxymethylpenicillanate in 600 ml. of methylene chloride cooled to 0°–5° C. The solution was then allowed to warm to room temperature and was stirred for 5 hrs. The solvent was removed in vacuo and the residue partitioned between 200 ml. of water and 200 ml. of ethyl acetate. The pH of the mixture was adjusted to 7 by the addition of a saturated sodium bicarbonate solution, and sufficient sodium bisulfite was added to give a negative peroxide test (starch-iodide). The layers were separated, and the aqueous washed with ethyl acetate. The organic layer and washings were combined, washed successively with water, 5% sodium bicarbonate solution and brine and dried over magnesium sulfate. Removal of the solvent under reduced pressure gave a foam, which on chromatographing on silica gel (chloroform-ethyl acetate 20:3) gave 3.5 g. of the desired intermediate product.

D. calcium 6β-hydroxymethylpenicillanate sulfone

To a 30 ml. solution of water-methanol (1:1) was added 3.5 g. of 5% palladium on calcium carbonate and the catalyst prehydrogenated at 47 psi in a hydrogenation apparatus. To the resulting catalyst was added 3.5 g. of benzyl 6β-hydroxymethylpenicillanate sulfone in 10 ml. of methanol and 20 ml. of tetrahydrofuran, and the mixture was shaken in a hydrogen atomsphere at 48 psi for 30 min. The catalyst was filtered through a filter aid and the filtrate concentrated in vacuo. The aqueous residue was extracted with ethyl acetate (2×100 ml.) and freeze dried to give 3.0 g. of the desired product as the calcium salt.

The NMR spectrum (CDCl$_3$-free acid) showed absorption at 1.49 (s, 3H), 1.6 (s, 3H), 4.1 (m, 3H), 4.32 (s, 1H) and 4.9 (d, 1H, J=4 Hz) ppm.

EXAMPLE 2

6β-[1(S)Hydroxyethyl]penicillanic Acid Sulfone

A. benzyl 6β-bromo-6α-[1(S)hydroxyethyl]pencillanate

To a stirred solution of 9 g. of benzyl 6,6-dibromopenicillanate in 200 ml. of dry toluene at −78° C. under argon was added dropwise 15 ml. of t-butyl lithium in pentane. The greenish-yellow solution was stirred 15 min. at −78° C., followed by the addition of 10 ml. of a 1 M solution of anhydrous zinc chloride in tetrahydrofuran. The mixture was stirred 45 min. at −78° C., and 5 ml. of acetaldehyde was added while maintaining the temperature at −78° C. After one hour of additional stirring, the reaction was quenched with 5 ml. of acetic acid in 50 ml. of ether at −78° C., and allowed to warm to room temperature. The toluene was removed in vacuo, and the residue partitioned between water and ethyl acetate. The organic phase was separated and the aqueous extracted (2×100 ml.) with ethyl acetate. The combined organic layers were washed with a 5% aqueous sodium bicarbonate solution followed by a saturated brine solution. They were then dried over magnesium sulfate and concentrated to an oil, which on chromatographing on silica gel, using toluene-ethyl acetate as the eluent (10:2), gave 3.5 g. of benzyl 6α-bromopenicillanate and 3.9 g. of the desired product. An analytical sample was purified by recrystallization from ether, m.p. 124°–125° C.

The NMR spectrum (CDCl$_3$) showed absorption at 1.42 (s, 3H), 1.45 (d, 3H, J=6 Hz), 1.67 (s, 3H), 2.55 (s, 1H), 4.3 (q, 1H, J=6 Hz), 4.6 (s, 1H), 5.3 (s, 2H), 5.5 (s, 1H) and 7.4 (s, 5H) at ppm.

B. benzyl 6β-[1-(S)Hydroxyethyl]penicillanate

To 20 ml. of methanol-water (1:1) was added 1.1 g. of 5% palladium-on-calcium carbonate, and the resulting mixture was hydrogenated at 47 psi. for 20 min. To the resulting black slurry was added 1.1 g. of benzyl 6β-bromo-6α-[1(S)hydroxyethyl]penicillanate and the hydrogenation continued at 47 psi. for 30 min. The spent catalyst was removed by filtration and the filtrate concentrated under reduced pressure. The pH of the residual aqueous was adjusted to 8, and extracted with methylene chloride. The organic phase was separated, dried over magnesium sulfate and evaporated to an oil. The residual oil was then chromatographed on 150 g. of silica gel using chloroform-ethyl acetate (10:1) as the eluent. Fractions 23 through 33 were combined and evaporated to dryness to give 148 mg. of the desired product.

The NMR spectrum (CDCl$_3$) showed absorption at 1.35 (d, 3H), 1.4 (s, 3H), 1.58 (s, 3H), 2.5 (m, 1H), 3.45 (dd, 1H, J=10, 4 Hz), 4.2 (m, 1H), 4.38 (s, 1H), 5.13 (s, 2H), 5.38 (d, 1H, J=4 Hz) and 7.33 (s, 5H) ppm.

C. benzyl 6β-[1(S)Hydroxyethyl]penicillanate sulfone

To a solution of 148 mg. of benzyl 6β-[1(S)hydroxyethyl]penicillanate in 20 ml. of methylene chloride at 0°–5° C. was added portionwise 223 mg. of m-chloroperbenzoic acid. The resulting reaction mixture was allowed to stir at room temperature overnight. The undissolved solids were filtered and the filtrate evaporated under reduced pressure to dryness. The residue was partitioned between a 5% aqueous sodium bicarbonate solution and ethyl acetate. Sodium bisulfite was added to the vigorously stirred mixture until a negative peroxide test (starch iodide) was obtained. The organic layer was subsequently separated and the aqueous layer extracted with additional ethyl acetate. The combined organic layers were successively backwashed with a saturated sodium bicarbonate solution and brine solution, and were then dried over magnesium sulfate. Removal of the solvent in vacuo gave 160 mg. of the product as an oil.

The NMR spectrum (CDCl$_3$) showed absorption at 1.27 (s, 3H), 1.35 (d, 3H, J=6 Hz), 1.5 (s, 3H), 3.2 (m, 1H), 3.85 (dd, 1H, J=11, 5 Hz), 4.53 (s, 1H), 4.77 (m, 1H), 4.77 (d, 1H, J=5 Hz), 5.28 (ABq, 2H, J=12 Hz) and 7.43 (s, 5H) ppm.

D. 6β-[1(S)hydroxyethyl]penicillanic acid sulfone

A suspension of 160 mg of 5% palladium-on-calcium carbonate in 20 ml. of methanol-water (1:1) was prehydrogenated at 47 psi. for 20 min. To the resulting suspension was added 160 mg. of benzyl 6β-[1(S)-hydroxyethyl]penicillanate sulfone and the hydrogenation continued at 51 psi. for one hour. The spent catalyst was filtered and the pH of the filtrate adjusted to 8. After the aqueous was extracted with ethyl acetate, the pH was adjusted to 1.8 and fresh ethyl acetate added. The ethyl acetate layer was separated, dried over magnesium sulfate and concentrated to an oil, 90 mg. The oil subsequently crystallized to give a white solid, m.p. 160°–161.5° C. dec.

The NMR spectrum (CDCl$_3$—DMSO—D$_6$) showed absorption at 1.2 (d, 3H, J=6 Hz), 1.42 (s, 3H), 1.52 (s, 3H), 3.80 (dd, 1H, J=10, 5 Hz), 4.28 (s, 1H), 4.5 (m, 1H) and 5.20 (d, 1H, J=5 Hz) ppm.

EXAMPLE 3

6β-[1(R)Hydroxyethyl]penicillanic Acid Sulfone

A. benzyl 6β-bromo-6α-[1(R)-hydroxyethyl]penicillanate

To 50 ml. of toluene cooled to −78° C. was added slowly 70 ml. of diethyl zinc, also cooled to −78° C. Subsequently, 45 g. of benzyl 6,6-dibromopenicillanate in 250 ml. of toluene was added to the reaction mixture over a period of 45 min. After one hour of stirring in the cold 17 ml. of acetaldehyde was added to the reaction mixture, and the stirring continued for one hour. The reaction was quenched by the addition of 11.5 ml. of acetic acid in 100 ml. of diethyl ether. The cooling bath was removed and the reaction allowed to warm to room temperature. An equal volume of water and ethyl acetate was added to the reaction mixture and allowed to stir for 5 min. The organic phase was subsequently separated and washed successively with water (3×75 ml.), a saturated sodium bicarbonate solution (3×75 ml.) and a saturate brine solution (1×100 ml.). The organic layer was dried over magnesium sulfate and evaporated in vacuo to an oil, which was chromatographed on 500 g. of silica gel using chloroform-ethyl acetate (10:1) as the eluent. Fractions 13 through 29 were combined and evaporated to dryness to give 20 g. of the crude intermediate product which was recrystallized from diethyl ether-hexane to give 12.7 g., m.p. 109°–110° C. The isolated material also contained benzyl 6β-bromo-6-α-[1(S)-hydroxyethyl]penicillanate.

B. benzyl 6β-[1(R)hydroxyethyl]penicillanate

A solution of 1.0 g. of benzyl 6β-bromo-6α-[1(R)hydroxyethyl]penicillanate and 1.4 ml. of tri-n-butyltin hydride in 35 ml. of benzene, under a nitrogen atmosphere was refluxed for 40 min. The reaction mixture was then cooled to room temperature and the solvent removed under reduced pressure. The residue was triturated repeatedly with hexane. The residue was chromatographed on 100 g. of silica gel using chloroform-ethyl acetate (20:1) as the eluent. Fractions 82 through 109 were combined and evaporated to give 750 ml. of the desired product.

The NMR spectrum (CDCl$_3$) showed absorption at 1.18 (d, 3H, J=6 Hz), 1.38 (s, 3H), 1.62 (s, 3H), 2.6 (n, 1H), 3.45 (dd, 1H, J=9, 4 Hz), 4.2 (m, 1H), 4.43 (s, 1H), 5.16 (s, 2H), 5.33 (d, 1H, J=4 Hz) and 7.33 (s, 5H) ppm.

C. benzyl 6β-[1(R)hydroxyethyl]penicillanate sulfone

A mixture of 335 mg. of benzyl 6β-[1(R)hydroxyethyl]penicillanate and 507 mg. of m-chloroperbenzoic acid in 50 ml. of methylene chloride is allowed to stir overnight at room temperature. The solids are filtered and the solvent removed from the filtrate. The residue is partitioned between 50 ml. of water and 50 ml. of ethyl acetate. Sodium bisulfite is added in portions to the stirred mixture until all the peroxide is destroyed as evidenced by a negative starch-iodide test. The organic phase is separated, dried over magnesium sulfate and the solvent removed in vacuo. The residue is utilized in the next step without further purification.

D. 6β-[1(R)hydroxyethyl]penicillanic acid sulfone

A suspension of 1.78 g. of 5% palladium-on-calcium carbonate in 40 ml. of methanol-water (1:1) is hydrogenated for 20 min. at 50 psi. Benzyl 6β-[1(R)hydroxyethyl]penicillanate sulfone (1.67 g.) is added to the resulting suspension and the hydrogenation continued at 50 psi for one hour. The methanol is removed under reduced pressure, and the aqueous residue extracted with ethyl acetate. The aqueous layer is acidified to pH 2 and extracted with ethyl acetate. The organic phase is washed with a saturated brine solution, dried over magnesium sulfate and concentrated to a white solid, 1.0 g., m.p. 182°–183° C. dec.

The NMR spectrum (DMSO - D$_6$) showed absorption at 1.15 (d, 3H, J=6 Hz), 1.37 (s, 3H), 1.47 (s, 3H), 3.87 (dd, 1H, J=10, 5 Hz), 4.28 (s, 1H), 4.5 (m, 1H), 5.11 (d, 1H, J=5 Hz) and 5.5 (m, 4H).

EXAMPLE 4

6β-[1(S)Hydroxyethyl]penicillanic Acid Sulfone

A. benzyl 6β-bromo-6α-[1(S)hydroxyethyl]penicillanate sulfone

To 500 ml. of methylene chloride, maintained at 5° C. under a nitrogen atmosphere, was added 14.7 g. of benzyl 6β-bromo-6α-[1(S)hydroxyethyl]penicillanate (Example 2A) and 17.8 g. of m-chloroperbenzoic acid, and the resulting reaction mixture allowed to stir overnight. An additional 200 mg. of the per acid is added and stirring continued for an additional 2.5 hrs. The reaction was filtered and the filtrate concentrated to a white solid. An equal volume of water-ethyl acetate was added to the residue and the pH adjusted to 7.4 with a saturated sodium bicarbonate solution. The organic phase was separated, added to fresh water and the pH adjusted to 8.2 with a saturated sodium bicarbonate solution. The ethyl acetate layer was backwashed with a saturated sodium bicarbonate solution (3×400 ml.) and then with a brine solution. The organic phase was separated, dried over magnesium sulfate and evaporated to an oil, 18.2 g.

The NMR spectrum (CDCl$_3$) showed absorption at 1.28 (s, 3H), 1.43 (d, 3H, J=6 Hz), 1.55 (s, 3H), 4.2 (q, 1H, J=6 Hz), 4.57 (s, 1H), 4.85 (s, 1H), 5.23 (ABq, 2H, J=12 Hz) and 7.38 (s, 5H) ppm.

B. benzyl 6β-[1(S)hydroxyethyl]penicillanate sulfone

To a solution of 740 mg. of benzyl 6β-bromo-6α-[1(S)hydroxyethyl]penicillanate sulfone in 10 ml. of benzene under a nitrogen atomsphere was added 0.52 ml. of tri-n-butyltin hydride, and the resulting mixture heated under reflux for 3 hrs. The benzene was removed in vacuo and the residue triturated with hexane. The hexane was decanted and the residue used in the next step without further purification.

C. 6β-[1(S)hydroxyethyl]penicillanic acid sulfone

One gram of 5% palladium-on-calcium carbonate in 20 ml. of water was prereduced with hydrogen at 50 psi. To the resulting slurry was added the crude benzyl 6β-[1(S)hydroxyethyl]penicillanate sulfone in 20 ml. of methanol from Example 4B, and hydrogenation continued for one hour at 50 psi. An additional 500 mg. of catalyst was added and the reaction continued for 45 min. The spent catalyst was filtered and the filtrate extracted (2×50 ml.) with ethyl acetate. The aqueous was over laid with fresh ethyl acetate on the pH adjusted to 1.5. The organic phase was separated and the aqueous extracted with ethyl acetate (7×100 ml.). The ethyl acetate acid extracts were combined, washed with a brined solution, dried over magnesium sulfate and concentrated in vacuo to dryness, 230 mg.

The NMR spectrum was identical to the product prepared in Example 2D.

EXAMPLE 5

6β-[1(R)Hydroxyethyl]penicillanic Acid Sulfone

A. benzyl 6β-bromo-6α-[1(R)hydroxyethyl]penicillanate

To a solution of 2.9 g. of benzyl 6β-bromo-6α-[1(R)-hydroxyethyl]penicillanate (Example 3A) in 100 ml. of methylene chloride cooled to 0°–5° C. was added 3.6 g. of m-chloroperbenzoic acid, and the resulting reaction mixture allowed to stir at room temperature overnight. The solvent was removed under reduced pressure and the residue dissolved in an equal volume of water-ethyl acetate. The pH of the mixture was adjusted to 7.4 with a saturated sodium bicarbonate solution and the organic layer separated. The organic phase was backwashed with a saturated brine solution, dried over magnesium sulfate and concentrated to an oil which crystallized, 4.0 g.

The NMR spectrum (CDCl$_3$) showed absorption at 1.25 (s, 3H), 1.28 (d, 3H, J=6 Hz), 1.5 (s, 3H), 2.9 (m, 1H), 3.7 (dd, 1H, J=10, 5 Hz), 4.43 (s, 1H), b 4.6 (m, 1H), 4.57 (d, 1H, J=5 Hz), 5.17 (ABq, 2H, J=12 Hz) and 7.32 (s, 5H) ppm.

B. benzyl 6β-[1(R)hydroxyethyl]penicillanate sulfone

A mixture of 3.0 g. of benzyl 6β-bromo-6α-[1(R)-hydroxyethyl]penicillanate sulfone and 2.9 ml. of tri-n-butyltin hydride in 100 ml. of benzene was refluxed under a nitrogen atmosphere for 30 min. The solvent was removed in vacuo and the residue extracted several times with hexane. The residual material was chromatographed on 250 g. of silica gel to give 1.67 g. of the desired product, which was used in the next step.

C. 6β-[1(R)hydroxyethyl]penicillanic acid sulfone

One and seven-tenths grams of 5% palladium-on-calcium carbonate in 40 ml. of 50% methanol-water was prereduced at 50 psi for 20 min. To the resulting suspension was added 1.67 g. of benzyl 6β-[1(R)hydroxyethyl]-penicillanate sulfone, and the hydrogenation continued for one hour. The catalyst was filtered and the methanol removed in vacuo from the filtrate. The aqueous residue was extracted with water, followed by the adjustment of the aqueous to 2.0. The acidified aqueous was extracted several times with ethyl acetate, and the combined extracts washed with a saturated brine solution and dried over magnesium sulfate. Removal of the solvent gave 1.0 g. of the product, which was indistinguishable in all respect from that prepared in Example 3D.

EXAMPLE 6

Starting with benzyl 6,6-dibromopenicillanate and the appropriate aldehyde and employing the procedures of Example 2, the following 6β-[1(S)hydroxyalkyl]-penicillanic acid sulfones are prepared:

6β-[1(S)hydroxypropyl]penicillanic acid sulfone; 6β-[1(S)hydroxy-n-butyl]penicillanic acid sulfone; 6β-[1(S)hydroxy-2-methylpropyl]penicillanic acid sulfone; 6β-[1(S)hydroxy-n-pentyl]penicillanic acid sulfone; 6β-[1(S)hydroxy-2-methyl-n-butyl]penicillanic acid sulfone; 6β-[1(S)hydroxy-3-methyl-n-butyl]penicillanic acid sulfone; and 6β-[1(S)hydroxy-2,2-dimethylpropyl]penicillanic acid sulfone.

EXAMPLE 7

Employing the procedures of Example 3, and starting with the requisite aldehyde and benzyl 6,6-dibromopenicillanate, the following compounds are prepared:

6β-[1(R)hydroxypropyl]penicillanic acid sulfone; 6β-[1(R)hydroxy-2-methylpropyl]penicillanic acid sulfone; β-[1(R)hydroxy-n-pentyl]penicillanic acid sulfone; 6β-[1(R)hydroxy-2-methyl-n-butyl]penicillanic acid sulfone; 6β-[1(R)hydroxy-3-methyl-n-butyl]-penicillanic acid sulfone; and 6β-[1(R)hydroxy-2,2-dimethylpropyl]penicillanic acid sulfone.

EXAMPLE 8

Starting with the appropriate benzyl 6-bromo-6-[1-hydroxy alkyl]penicillanate and employing the procedures of Example 4/5, the following 6β-compounds are prepared:

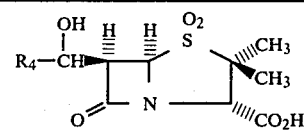

| R$_4$ | * |
|---|---|
| CH$_3$CH$_2$— | (S) |
| CH$_3$CH$_2$— | (R) |
| CH$_3$(CH$_2$)$_2$— | (R) |
| CH$_3$(CH$_2$)$_3$— | (S) |
| CH$_3$(CH$_2$)$_3$— | (R) |
| CH$_3$CH(CH$_3$)CH$_2$— | (S) |
| (CH$_3$)$_3$C— | (R) |
| (CH$_3$)$_3$C— | (S) |

EXAMPLE 9

6β-[1(S)Hydroxybenzyl]penicillanic Acid Sulfone and 6β-[1(R)Hydroxybenzyl]penicillanic Acid Sulfone

A. benzyl 6α-bromo-6β-[1(R) and (S)hydroxybenzyl]penicillanate

To a solution of 9.0 g. of benzyl 6,6-dibromopenicillanate in 200 ml. of dry toluene cooled to −78° C. and maintained under an argon atmosphere was added 14 ml. of t-butyl lithium cooled to −67° C. After stirring in the cold for 45 min. 2 ml. of benzaldehyde was added and the reaction mixture allowed to stir for one hour. A solution of 1.2 ml. of acetic acid in 50 ml. of diethyl ethyl was then added over a period of 10 min. and the mixture stirred at −78° C. for 30 min. Water (100 ml.) and diethyl ethyl (100 ml.) were added and the mixture stirred at room temperature for 30 min. The organic layer was separated and the aqueous washed with ether. The organic layer and the ether washings were combined and washed successively with water (1×50 ml.), a saturated aqueous sodium bicarbonate solution (2×50 ml.) and a saturated brine solution. The organic phase was dried over magnesium sulfate and concentrated to give 10.3 g. of an oil.

The residual material was chromatographed on 450 g. of silica gel using chloroform-ethyl acetate (20:1) as the eluent. Fractions 71 through 101 were combined and concentrated to give 1.97 g. of the product as a semi-solid.

B. benzyl 6β-[1(R)hydroxybenzyl]penicillanate and benzyl 6β-[1(S)hydroxybenzyl]penicillanate A solution of 1.9 g. of benzyl 6α-bromo-6β-[1(R) and (S)hydroxybenzyl]penicillanate and 1.1 ml. of tri-n-butyltin hydride in 30 ml. of dry benzene under a nitrogen atmosphere was refluxed 3.5 hrs. An additional 1.0 ml. of hydride was added and the refluxing continued overnight. The benzene was removed in vacuo and the residue was slurried with hexane. The hexane was decanted and the 850 mg. of residual oil chromatographed on 100 g. of silica gel using chlroform-ethyl acetate (20:3) as the eluent. Fractions 20 thru 34 were combined and the solvent removed to give 495 mg. of benzyl 6β-[1(R)hydroxybenzyl]penicillanate.

The NMR specturm (CDCl$_3$) showed absorption at 1.42 (s, 3H), 1.67 (s, 3H), 3.2 (m, 1H), 3.9 (dd, 1H, J=4, 10 Hz), 4.42 (s, 1H), 5.2 (s, 2H), 5.2 (m, 1H), 5.4 (d, 1H, J=4 Hz) and 7.35 (m, 10H) ppm.

Fractions 35 thru 58 were combined and concentrated in vacuo to give 380 mg. of benzyl 6β-[1(S)hydroxybenzyl]-penicillanate.

The NMR spectrum (CDCl$_3$) showed absorption at 1.33 (s, 3H), 1.67 (s, 3H), 3.4 (m, 1H), 3.85 (dd, 1H, J=4, 10 Hz), 4.42 (s, 1H), 5.10 (d, 1H, J=4 Hz), 5.10 (s, 2H), 5.10 (m, 1H) and 7.35 (m, 10H) ppm.

C. benzyl 6β-[1(R)hydroxybenzyl]penicillanate sulfone

To a solution of 490 mg. of benzyl 6β-[1(R)hydroxybenzyl]penicillanate in 50 ml. of methylene chloride cooled to −5° C. was added 1.35 g. of m-chloroperbenzoic acid, and the resulting reaction mixture allowed to stir overnight. The solvent is removed in vacuo and the residue treated with an equal volume of ethyl acetate and water. The pH of the mixture is adjusted to 7.2 with a saturated sodium bicarbonate solution and sufficient sodium bisulfite was added to decompose the excess per acid (negative starch iodide test). The organic phase was separated and washed successively with water at a pH of 8.2, a saturated sodium bicarbonate solution and a brine solution. The organic layer was separated, dried over magnesium sulfate and concentrated to 395 mg. of a white solid. The product was chromatographed on 100 g. of silica gel using toluene-ethyl acetate (10:12) as the eluent. Fractions 18 thru 27 were combined and concentrated to give 148 mg. of the product as an oil.

The NMR spectrum (CDCl$_3$) showed absorption at 1.22 (s, 3H), 1.5 (s, 3H), 2.6 (m, 1H), 4.07 (dd, 1H, J=10, 5 Hz), 4.47 (s, 1H), 4.67 (d, 1H, J=5 Hz), 5.2 (ABq, 2H), 5.63 (d, 1H, J=10 Hz) and 7.37 (m, 10 H) ppm.

C'. benzyl 6β-[1(S)hydroxybenzyl]penicillanate sulfone

The procedure of Example 9C was repeated starting with benzyl 6β-[1(S)hydroxybenzyl]penicillanate to give the desired product.

The NMR spectrum (CDCl$_3$) showed absorption at 1.19 (s, 3H), 1.5 (s, 3H), 2.8 (m, 1H), 4.20 (dd, 1H, J=10, 5 Hz), 4.38 (d, 1H, J=5 Hz), 4.43 (s, 1H), 5.20 (ABq, 2H), 5.77 (d, 1H, J=10 Hz) and 7.37 (m, 10H) ppm.

D. 6β-[1(R)hydroxybenzyl]penicillanic acid sulfone

To a suspension of 148 mg. of 5% palladium on calcium carbonate in 20 ml. of water-methanol (1:1) which had been prehydrogenated at 47.5 psi for 20 min. was added 140 mg. of benzyl 6β-[1(R)hydroxybenzyl]-penicillante sulfone and the hydrogenation continued at an initial pressure of 47 psi for 40 min. An additional 140 mg. of catalyst was added and the reduction continued for 30 min. A final 140 mg. of catalyst was then added and the reduction continued for an additional 30 min. The spent catalyst was filtered and the filtrate extracted with ethyl acetate. The aqueous layer was separated, the pH adjusted to 1.5 and fresh ethyl acetate added. The ethyl acetate extract was back-washed with a brine solution and dried over magnesium sulfate. Removal of the solvent in vacuo gave 90 mg. of the product as an oil.

The NMR spectrum (CDCl$_3$) showed absorption at 1.50 (s, 3H), 1.67 (s, 3H), 4.1 (dd, 1H, J=10, 5 Hz), 4.45 (s, 1H), 4.78 (d, 1H, J=5 Hz), 5.7 (d, 1H, J=10 Hz) and 7.4 (m, 5H).

D'. 6β-[1(S)hydroxybenzyl]penicillanic acid sulfone

To a suspension of 170 mg. of prereduced 5% palladium-on-calcium carbonate in 20 ml. of water-methanol (1:1) was added 170 mg. of benzyl 6β-[1(S)hydroxybenzyl]-penicillanate sulfone and the hydrogenation continued at 47 psi for 40 min. An additional 340 mg. of catalyst was added and the reduction was continued for 3 hrs. The catalyst was filtered, washed with tetrahydrofuran-water (1:1) and the combined filtrate and washings concentrated. The residual water was extracted with ethyl acetate followed by acidification of the aqueous layer to pH 1.5 and subsequent extraction with fresh ethyl acetate. The organic phase was back-washed with a brine solution and dried over magnesium sulfate. Removal of the solvent in vacuo gave 100 mg. of the product, m.p. 164°–165° C. dec.

The NMR spectrum (CDCl$_3$) showed absorption at 1.40 (s, 3H), 1.55 (s, 3H), 4.0 (dd, 1H, J=5, 10 Hz), 4.4 (d, 1H, J=5 Hz), 4.4 (s, 1H), 5.7 (d, 1H, J=10 Hz), and 7.4 (m, 5H) ppm.

EXAMPLE 10

6β-[1(S)Hydroxy-2-phenethyl]penicillanic Acid Sulfone and

6β-[1(R)Hydroxy-2-phenethyl]penicillanic Acid Sulfone

A. benzyl 6α-bromo-6β-[1(R)Hydroxy-2-phenethyl]penicillanate and benzyl 6β-bromo-6α-[1(S)hydroxy-2-phenethyl]penicillanate To a solution of 9.0 g. of benzyl 6,6-dibromopenicillanate in 200 ml. of toluene cooled to −78° C. and maintained under an argon atmosphere was added 9.2 ml. of a 2.5 M solution of t-butyl lithium, and the resulting reaction mixture allowed to stir for 40 min. Subsequently, 2.34 ml. of phenylacetaldehyde was added. After stirring for one hour, 1.2 ml. of acetic acid in 25 ml. of diethyl ether was added and the stirring continued at −78° C. for 30 min. The reaction mixture was allowed to warm to room temperature after which an equal volume of water was added. The organic layer was separated and saved, and the aqueous was extracted with ethyl acetate. The organic layer and extracts were combined, washed successively with water, a saturated sodium bicarbonate solution and a brine solution and dried over magnesium sulfate. The oil residue, 11.0 g., which remained after the solvent was removed in vacuo was chromatographed on 500 g. of silica gel using chloroform-ethyl acetate (20:0.2) as the eluent.

Fractions 150 thru 154 were combined and concentrated to give 670 mg. of benzyl 6α-bromo-6β-[1(R)hydroxy-2-phenethyl]pencillanate.

The NMR spectrum (CDCl₃) showed absorption at 1.35 (s, 1H), 1.53 (s, 1H), 2.85 (m, 3H), 4.23 (m, 1H), 4.41 (s, 1H), 5.13 (s, 2H), 5.57 (s, 1H) and 7.33 (m, 10H) ppm.

Fractions 155 thru 195 were combined and concentrated to give 4.84 g. of benzyl 6β-bromo-6α-[1(S)hydroxy-2-phenethyl]penicillanate.

The NMR spectrum (CDCl₃) showed absorption at 1.35 (s, 3H), 1.60 (s, 3H), 2.85 (m, 3H), 4.23 (m, 1H), 4.41 (s, 1H), 5.08 (s, 2H), 5.42 (s, 1H) and 7.33 (m, 10H) ppm.

B. benzyl 6β-[1(R)hydroxy-2-phenethyl]penicillanate and benzyl 6β-(1(S)hydroxy-2-phenethyl]penicillanate A benzene solution (80 ml.) containing 5.51 g. of benzyl 6α-bromo-6β-[1(R)hydroxy-2-phenethyl]-penicillanate and benzyl 6β-bromo-6α-[1(S)hydroxy-2-phenethyl]penicillanate, as isolated in Example 10A, was treated with 3.2 ml. of tri-n-butyltin hydride, and the reaction heated to reflux under a nitrogen atmosphere for 4 hrs. The solvent was removed under reduced pressure and the residue washed several times with hexane. The residue, 4.2 g., was chromatographed on 500 g. of silica gel using chloroform-ethyl acetate (20:3) as the eluent.

Fraction 50 thru 61 were combined and concentrated to give 596 mg. of benzyl 6β-[1(S)hydroxy-2-phenethyl]penicillanate.

The NMR spectrum (CDCl₃) showed absorption at 1.35 (s, 3H), 1.69 (s, 3H), 2.8 (m, 2H), 3.1 (m, 1H), 3.55 (dd, 1H, J=4, 10 Hz), 4.23 (m, 1H), 4.40 (s, 1H), 5.15 (s, 1H), 5.35 (d, 1H, J=4 Hz), 7.22 (s, 5H) and 7.3 (s, 5H) ppm.

Fractions 65 thru 75 were combined and concentrated to give 1.5 g. of benzyl 6β-[1(R)hydroxy-2-phenethyl]penicillanate.

The NMR spectrum (CDCl₃) showed absorption at 1.35 (s, 3H), 1.6 (s, 3H), 2.78 (m, 2H), 2.9 (m, 1H), 3.43 (dd, 1H, J=5.9 Hz), 4.30 (m, 1H), 4.40 (s, 1H), 5.12 (s, 1H), 5.22 (d, 1H, J=5 Hz), 7.19 (s, 5H) and 7.3 (s, 5H) ppm.

C. benzyl 6β-[1(S)hydroxy-2-phenethyl]penicillanate sulfone

To a cooled (0°–5° C.) solution of 300 mg. of benzyl 6β-[1(S)hydroxy-2-phenethyl]penicillanate in 50 ml. of methylene chloride was added 630 mg. of m-chloroperbenzoic acid, and the resulting reaction mixture allowed to stir overnight. The solvent was removed in vacuo and the residue treated with an equal volume of water and ethyl acetate. The pH of the mixture was adjusted to 7.2 with a saturated sodium bicarbonate solution, and sufficient sodium bisulfite was added to give a negative starch-iodide test. The organic phase was separated treated with an equal volume of water and the pH adjusted to 8.2 as above. The organic phase was separated, washed with a brine solution and dried over magnesium sulfate. Removal of the solvent gave the product as an oil, 320 mg.

The NMR spectrum (CDCl₃) showed absorption at 1.22 (s, 1H), 1.5 (s, 1H), 2.8 (m, 2H), 3.8 (dd, 1H, J=5, 10 Hz), 4.42 (s, 1H), 4.6 (d, 1H, J=5 Hz), 4.75 (m, 1H) 5.18 (ABq, 2H), 7.2 (s, 5H) and 7.3 (s, 5H) ppm.

C'. benzyl 6β-[1(R)hydroxy-2-phenethyl]penicillanate sulfone

Using the procedure of Example 10C, and starting with 700 mg. of benzyl 6β-[1(R)hydroxy-2-phenethyl]-penicillanate and 850 mg. of m-chloroperbenzoic acid there was obtained 610 mg. of the desired product as an oil.

The NMR spectrum (CDCl₃) showed absorption at 1.25 (s, 1H), 1.52 (s, 1H), 2.8 (m, 2H), 3.7 (dd, 1H, J=5, 10 Hz), 4.42 (s, 1H), 4.55 (d, 1H, J=5 Hz, 4.80 (m, 1H), 5.18 (ABq, 2H), 7.22 (s, 5H) and 7.3 (s, 5H) ppm.

D. 6β-[1(R)hydroxy-2-phenethyl]penicillanic acid sulfone sodium salt

To a suspension of 600 mg. of 5% palladium-on-calcium carbonate, pre-hydrogenated at 47 psi for 20 min., in 20 ml. of water-methanol (1:1) was added 600 mg. of benzyl 6β-[1(R)hydroxy-2-phenethyl]penicillanate sulfone. After continuing the hydrogenation for 35 min. at 48 psi, an additional 600 mg. of catalyst was added and the hydrogenation at 48 psi continued for 10 min. The spent catalyst was filtered and washed with water-methanol (1:1). The filtrate and washings were combined and the methanol removed under reduced pressure. The residual aqueous (pH 8.0) was extracted with ethyl acetate and the layers separated. The aqueous layer was acidified to pH 1.8 and extracted with ethyl acetate. The organic phase was separated, backwashed with a brine solution and dried over magnesium sulfate. Removal of the solvent in vacuo gave 390 mg. of the product as a white solid.

The free acid was dissolved in ethyl acetate containing a small amount of diethyl ether. To this solution was added 177 mg. of sodium 2-ethylhexanoate, and the solution allowed to stir for one hour. The precipitated solid sodium salt of the product was filtered and dried, 250 mg., m.p. 205°–208° C. dec.

The NMR spectrum (D₂O) showed absorption at 1.42 (s, 3H), 1.65 (s, 3H), 2.9 (m, 2H), 4.0 (dd, 1H, J=5, 10 Hz), 4.3 (s, 1H), 4.9 (m, 1H), 5.0 (d, 1H, J=5 Hz) and 7.3 (s, 5H) ppm.

D'. 6β-[1(S)hydroxy-2-phenethyl]penicillanic acid sulfone

To a suspension of 320 mg. of prereduced 5% palladium-on-calcium carbonate in 20 ml. of water-methanol (1:1) was added 320 mg. of benzyl 6β-[1(S)hydroxy-2-phenethyl]penicillanate sulfone, and the resulting mixture was shaken in a hydrogen atmosphere at an initial pressure of 47 psi for 30 min. The catalyst was filtered, washed with water-methanol, and the washings and filtrate were combined. The aqueous residue remaining after the methanol was removed in vacuo was extracted with ethyl acetate and was then extracted with fresh ethyl acetate. The extract was backwashed with a brine solution, dried over magnesium sulfate and evaporated to an oil, 80 mg., which solidified, m.p. 80°–85° C. dec.

The NMR spectrum (CDCl₃) showed absorption at 1.42 (s, 1H), 1.65 (s, 1H), 2.9 (m, 2H), 4.0 (dd, 1H, J=5, 10 Hz), 4.3 (s, 1H), 4.8 (m, 1H), 4.85 (d, 1H, J=5 Hz) and 7.3 (s, 5H) ppm.

EXAMPLE 11

6β-[1(R)Hydroxy-3-phenylpropyl]penicillanic Acid Sulfone and
6β-[1(S)Hydroxy-3-phenylpropyl]penicillanic Acid Sulfone A. benzyl 6α-bromo-6β-[1(R) and (S)hydroxy-3-phenylpropyl]penicillanate Benzyl 6,6-dibromopenicillanate (4.5 g.) was dissolved in 100 ml. of dry toluene and the resulting solution cooled to −70° C. To the cooled solution was added 7.3 ml. of t-butyl lithium. After stirring in the cold for 20 min. 1.3 ml. of hydrocinnamaldehyde was added and stirring continued for 20 min. Acetic acid (0.57 ml.) was added and the reaction mixture allowed to warm to room temperature. The toluene was removed in vacuo and an equal volume of chloroform and water were added. The organic phase was separated, backwashed with a brine solution and dried over magnesium sulfate. Removal of the solvent gave 5.3 g. of the product as an oil. The product was purified by chromatographing on silica gel using chloro-form ethyl acetate (20:1) as the eluent.

Fractions 88 thru 155 were combined and the solvent removed in vacuo to give 3.2 g. of the product.

Anal. Calc'd for $C_{24}H_{20}O_4NSBr$: C, 57.2; H, 5.2; N, 2.8. Found: C, 56.5; H, 5.2; N, 2.9.

B. benzyl 6β-[1(R)hydroxy-3-phenylpropyl]penicillanate and benzyl 6β-[1(S)hydroxy-3-phenylpropyl]penicillanate A solution of 1.5 g. of benzyl 6α-bromo-6β-[1(R) and (S)hydroxy-3-phenylpropyl]penicillanate and 1.72 ml. of tri-n-butyltin hydride in 100 ml. of benzene was refluxed under a nitrogen atmosphere for 2 hrs. and 40 min. The solvent was removed in vacuo and the residue (3.7 g.) chromatographed on 150 g. of silica gel using chloroform-ethyl acetate (20:1) as the eluent.

Fractions 63–80 were combined and the solvent removed to give 244 mg. of benzyl 6β-[1(S)hydroxy-3-phenylpropyl]penicillanate as an oil.

The NMR spectrum (CDCl$_3$) showed absorption at 1.40 (s, 3H), 1.50 (s, 3H), 1.8 (m, 2H), 2.8 (m, 3H), 3.59 (dd, 1H, J=4, 10 Hz), 4.1 (m, 1H), 4.43 (s, 1H), 5.20 (s, 2H), 5.43 (d, 1H, J=4 Hz), 7.25 (s, 5H) and 7.4 (s, 5H) ppm.

Fractions 114–133 were combined and the solvent evaporated to give 369 mg. of benzyl 6β-[1(R)hydroxy-3-phenylpropyl]penicillanate as an oil.

The NMR spectrum (CDCl$_3$) showed absorption at 1.38 (s, 3H), 1.60 (s, 3H), 1.8 (m, 2H), 2.8 (m, 3H), 3.55 (dd, 1H, J=4,9 Hz), 4.1 (m, 1H), 4.43 (s, 1H), 5.20 (s, 2H), 5.35 (d, 1H, J=4 Hz), 7.25 (s, 5H) and 7.4 (s, 5H) ppm.

C. benzyl 6β-[1(R)hydroxy-3-phenylpropyl]penicillanate sulfone

To a solution of 585 mg. of benzyl 6β-[1(R)hydroxy-3-phenylpropyl]penicillanate in 35 ml. of methylene chloride cooled to 0°–5° C. was added 700 mg. of m-chloroperbenzoic acid, and the reaction mixture allowed to stir overnight. The solvent was removed under reduced pressure and the residue treated with an equal volume of water and ethyl acetate. The pH was adjusted to 7.2 with a saturated sodium bicarbonate solution and the organic layer separated. An equal volume of water was added to the ethyl acetate layer and the pH again adjusted as above to 8.4. The ethyl acetate layer was separated, washed with a saturated sodium bicarbonated solution (3×50 ml.) and a brine solution, and was then dried over magnesium sulfate. Removal of the solvent gave 678 mg. of the product as an oil which crystallized on standing, m.p. 142°–143° C.

The NMR spectrum (CDCl$_3$) showed absorption at 1.30 (s, 3H), 1.6 (s, 3H), 1.8 (m, 2H), 2.8 (m, 2H), 3.83 (dd, 1H, J=5,9 Hz), 4.50 (s, 1H), 4.55 (d, 1H, J=5 Hz), 4.75 (m, 1H), 5.2 (ABq, 2H), 7.2 (s, 5H) and 7.38 (s, 5H) ppm.

C′. benzyl 6β-[1(S)hydroxy-3-phenylpropyl]penicillanate sulfone

The procedure of Example 11C was followed, starting with 300 mg. of benzyl 6β-[1(S)hydroxy-3-phenylpropyl]penicillanate and 361 mg. of m-chloroperbenzoic acid in 35 ml. of methylene chloride to give 346 mg. of product as an oil.

The NMR spectrum (CDCl$_3$) showed absorption at 1.28 (s, 3H), 1.52 (s, 1H), 1.8 (m, 2H), 2.80 (m, 2H), 3.9 (dd, 1H, J=5,10 Hz), 4.45 (s, 1H), 4.62 (m, 1H), 4.67 (d, 1H, J=5 Hz), 5.22 (ABq, 2H), 7.22 (s, 5H), and 7.38 (s, 5H) ppm.

D. 6β-[1(R)hydroxy-3-phenylpropyl]penicillanic acid sulfone

Benzyl 6β-[1(R)hydroxy-3-phenylpropyl]penicillanate sulfone (678 mg.) was added to a suspension of 700 mg. of prehydrogenated 5% palladium-on-calcium carbonate in 20 ml. of water-methanol (1:1). The mixture was shaken in a hydrogen atmosphere at an initial pressure of 52 psi for one hour. At that time an additional 700 mg. of catalyst was added and the hydrogenation continued for one hour. The catalyst was filtered and washed with water-methanol. The washings and filtrate were combined and the methanol removed in vacuo. The aqueous residue was extracted with ethyl acetate, followed by the adjustment of the pH of the aqueous to 1.5 and extraction with fresh ethyl acetate. The organic phase was backwashed with a brine solution and dried over magnesium sulfate. Removal of the solvent gave 304 mg., m.p. 138°–140° C. dec.

A sample of the free acid (190 mg.) was dissolved in ethyl acetate and was subsequently treated with 99 mg. of sodium 2-ethylhexanoate. After stirring overnight the sodium salt of the desired product was filtered and dried, 165 mg.

The NMR spectrum (DMSO-D$_6$) of the free acid showed absorption at 1.45 (s, 1H), 1.53 (s, 1H), 1.8 (m, 2H), 2.80 (m, 2H), 3.85 (dd, 1H, J=5,9 Hz), 4.35 (s, 1H), 4.60 (d, 1H, J=5 Hz), 4.75 (m, 1H) and 7.23 (s, 5H) ppm.

D′. 6β-[1(S)hydroxy-3-phenylpropyl]penicillanic acid sulfone

The procedure of Example 11D was repeated starting with 346 mg. of benzyl 6β-[1(S)hydroxy-3-phenylpropyl]penicillanate sulfone and 350 mg. of 5% palladium-on-calcium carbonate in 20 ml. of water-methanol (1:1) to give 196 mg. of the desired product, m.p. 146°–148° C. dec.

A sample of 126 mg. of 6β-[1(S)hydroxy-3-phenylpropyl]penicillanic acid sulfone was dissolved in a small amount of ethyl acetate, and was subsequently treated with 57 mg. of sodium 2-ethylhexanoate. Some diethyl ether was added and the resulting precipitate was filtered and dried to give 57 mg. of the sodium salt of the desired product.

The NMR spectrum (DMSO-D$_6$) of the free acid showed absorption at 1.47 (s, 1H), 1.60 (s, 1H), 2.0 (m, 2H), 2.8 (m, 2H), 3.9 (dd, 1H, J=5,10 Hz), 4.40 (s, 1H), 4.67 (m, 1H), 4.70 (d, 1H) and 7.2 (s, 5H) ppm.

EXAMPLE 12

6β-[1(R)Hydroxy-1-(2'-pyridyl)methyl]penicillanic Acid Sulfone and

6β-[1(S)Hydroxy-1-(2'-pyridyl)methyl]penicillanic Acid Sulfone

A. benzyl 6β-[1(R) and (S)hydroxy-1-(2'-pyridyl)methyl]penicillanate

To a cooled (−78° C.) solution of 9.0 g. of benzyl 6,6-dibromopenicillanate in 200 ml. of toluene under an argon atmosphere was added 11.8 ml. of t-butyl lithium and the resulting green solution allowed to stir for 30 min. 2-Pyridylcarboxaldehyde (1.9 ml.) was added and the reaction mixture stirred in the cold for 45 min. Subsequently 1.2 ml. of acetic acid was added in 25 ml. of diethyl ether over a period of 20 min. The mixture was allowed to stir in the cold for 30 min. and was then allowed to warm to 10° C. The reaction mixture was chromatographed on a Florisil column using toluene-ethyl acetate (2:1) as the eluent. Fractions (300 ml. each) 3 thru 5 were combined and evaporated to give 4.8 g. of an oil.

The oil was dissolved in 60 ml. of dry benzene to which was then added 3.2 ml. of tri-n-butyltin hydride. The resulting reaction mixture was then refluxed under a nitrogen atmosphere for 2.5 hours. An additional 2.0 ml. of hydride was added and the heating continued overnight. The benzene was removed in vacuo and the residue slurried in hexane several times. The remaining oil was chromatographed on 500 g. of silica gel using toluene-ethyl acetate (2:1) as the eluent.

Fractions 104 thru 131 were combined and the solvent removed under reduced pressure to give 480 mg. of benzyl 6β-[1(R)hydroxy-1-(2'-pyridyl)methyl]penicillanate as an oil.

The NMR spectrum (CDCl$_3$) showed absorption at 1.45 (s, 3H), 1.73 (s, 3H), 3.87 (dd, 1H, J=4, 10 Hz), 4.53 (s, 1H), 4.65 (m, 1H), 5.20 (m, 1H), 5.23 (s, 2H), 5.48 (d, 1H, J=4 Hz), 7.4 (s, 5H), 7.5 (m, 3H) and 8.6 (m, 1H) ppm.

Fractions 136 thru 190 were combined and the solvent removed in vacuo to give 950 mg. of benzyl 6β-[1(S)hydroxy-1-(2'-pyridyl)methyl]penicillanate as an oil.

The NMR spectrum (CDCl$_3$) showed absorption at 1.40 (s, 3H), 1.68 (s, 3H), 4.0 (m, 1H), 4.05 (dd, 1H, J=4.9 Hz), 4.55 (s, 1H), 5.2 (s, 2H), 5.22 (m, 1H), 5.46 (d, 1H, J=4 Hz), 7.3 (s, 5H), 7.4 (m, 3H) and 8.5 (m, 1H) ppm.

B. benzyl 6β-[1(R)hydroxy-1-(2'-pyridyl)methyl]penicillanate sulfone

Under a nitrogen atmosphere 500 mg. of m-chloroperbenzoic acid was added to a solution of 480 mg. of benzyl 6β-[1(R)hydroxy-1-(2'-pyridyl)methyl]penicillanate in 40 ml. of methylene chloride cooled to 0°–5° C. After stirring for one hour, the solvent was removed in vacuo and the residue treated with an equal volume of water and ethyl acetate. The pH was adjusted to 7.2 with a saturated sodium bicarbonate solution followed by addition of sufficient sodium bisulfite until a negative starch-iodide test was given. After the aqueous layer was separated and fresh ethyl acetate was added, the pH was raised, as above, to 8.2. The ethyl acetate layer was separated, backwashed with a sodium bicarbonate solution and a brine solution and dried over magnesium sulfate. Removal of the solvent gave 480 mg. of an oil, which was subsequently chromatographed on 50 g. of silica gel using ethyl acetate as the eluent. Fractions 22 thru 55 were combined and the solvent removed in vacuo to give 125 mg. of the product.

The NMR spectrum (CDCl$_3$) showed absorption at 1.22 (s, 3H), 1.50 (s, 3H), 4.40 (s, 1H), 4.79 (m, 1H), 4.80 (d, 1H, J=4 Hz), 5.18 (ABq, 2H, J=12 Hz), 5.6 (m, 1H), 7.2 (m, 3H), 7.25 (s, 5H) and 8.1 (m, 1H) ppm.

B'. benzyl 6β-[1(S)hydroxy-1-(2'-pyridyl)methyl]penicillanate sulfone

Starting with 250 mg. of benzyl 6β-[1(S)hydroxy-1-(2'-pyridyl)methyl]penicillanate and 320 mg. of m-chloroperbenzoic acid in 25 ml. of methylene chloride, and following the procedure of Example 12B, gave 240 mg. of the desired product as a white solid, m.p. 140°–145° C.

The NMR spectrum (CDCl$_3$) showed absorption at 1.23 (s, 3H), 1.59 (s, 3H), 4.6 (s, 1H), 4.8 (m, 2H), 5.3 (ABq, 2H, J=12 Hz), 5.95 (m, 1H), 7.4 (s, 5H), 7.5 (m, 3H) and 8.4 (m, 1H) ppm.

C. 6β-[1(R)hydroxy-1-(2'-pyridyl)methyl]penicillanic acid sulfone

To a suspension of 120 mg. of prereduced 5% palladium-on-calcium carbonate in 20 ml. of methanol-water (1:1) was added 120 mg. of benzyl 6β-[1(R)hydroxy-1-(2'-pyridyl)methyl]penicillanate sulfone, and the mixture was shaken in a hydrogen atmosphere at an initial pressure 47 psi for 30 min. An additional 120 mg. of catalyst was added and the hydrogenation continued for 45 min. at 47 psi. The catalyst was filtered, washed with methanol-water and the washings and filtrate combined. The methanol was removed in vacuo and the aqueous residue extracted with ethyl acetate. The aqueous layer was freeze dried to give 90 mg. of the desired product as the calcium salt.

The NMR spectrum (D$_2$O) of the calcium salt showed absorption at 1.50 (s, 3H), 1.65 (s, 3H), 4.35 (s, 1H), 4.70 (m, 1H), 5.18 (d, 1H, J=4 Hz), 5.65 (d, 1H, J=11 Hz), 7.7 (m, 3H) and 8.6 (broad d, 1H, J=Hz) ppm.

C'. 6β-[1(S)hydroxy-1-(2'-pyridyl)methyl]penicillanic acid sulfone

The procedure of Example 12C was repeated, starting with 240 mg. of benzyl 6β-[1(S)hydroxy-1-(2'-pyridyl)methyl]penicillanate and 480 mg. of palladium-on-calcium carbonate in 20 ml. of methanol water, to give 170 mg. of the calcium salt of the desired product.

EXAMPLE 13

Starting with benzyl 6,6-dibromopenicillanate and the appropriate pyridylcarboxaldehyde, and employing the procedures of Example 12, the following compounds are prepared:

6β-[1(R)hydroxy-1-(3'-pyridyl)methyl]penicillanic acid sulfone; 6β-[1(R)hydroxy-1-(4'-pyridyl)methyl]penicillanic acid sulfone; 6β-[1(S)hydroxy-1-(4'-pyridyl)methyl]penicillanic acid sulfone; and 6β-[1(S)hydroxy-1-(3'-pyridyl)methyl]penicillanic acid sulfone.

EXAMPLE 14

6β-Acetoxymethylpenicillanic Acid Sulfone

A. benzyl 6β-acetoxymethylpenicillanate sulfone

To a solution of 500 mg. of benzyl 6β-hydroxymethylpenicillanate sulfone and 0.196 ml. of triethylamine in 20 ml. of methylene chloride cooled to 0°–5° C. was added 0.1 ml. of acetyl chloride and 10 mg. of 4-dimethylaminopyridine. After stirring for 20 min. the solvent was removed in vacuo and ethyl acetate was added to the residue. The resulting solids were filtered, and the filtrate washed successively with water, water at p 1.0, a saturated sodium bicarbonate solution and a brine solution. The organic phase was dried over magnesium sulfate and the solvent removed in vacuo to give 600 mg. of product as an oil.

Th NMR spectrum (CDCl$_3$) showed absorption at 1.30 (s, 3H), 1.59 (s, 3H), 2.1 (s, 3H), 4.2 (m, 1H), 4.5 (s, 1H), 4.6 (m, 2H), 3.65 (d, 1H, J=Hz), 5.22 (ABq, 2H, J=12 Hz) and 7.4 (s, 5H) ppm.

B. 6β-acetoxymethylpenicillanic acid sulfone

To a suspension of 600 mg. of 5% palladium-on-calcium carbonate, prereduced in 20 ml. of water-hydrogen to 50 psi for 20 min. was added 600 mg. of benzyl 6β-acetoxymethylpenicillanic acid sulfone. The resulting mixture was shaken in a hydrogen atmosphere at an initial pressure of 50 psi for 45 min. The catalyst was filtered and washed with methanol-water. The filtrate and washings were combined and freeze dried to give 360 mg. of the desired product as a calcium salt.

The NMR spectrum (D$_2$O) of the calcium salt showed absorption at 1.5 (s, 3H), 1.61 (s, 3H), 2.18 (s, 3H), 4.25 (s, 1H), 4.3 (m, 1H), 4.60 (m, 2H) and 5.07 (d, 1H, J=4 Hz) ppm.

EXAMPLE 15

6β-Stearoyloxymethylpenicillanic Acid Sulfone

A. benzyl 6β-stearoyloxymethylpenicillanate sulfone

Starting with 500 mg. of benzyl 6β-hydroxymethylpenicillanate sulfone, 430 mg. of stearoyl chloride, 0.196 ml. of triethylamine and 10 mg. of 4-dimethylaminopyridine, and following the procedure of Example 14A, there was obtained 784 mg. of the desired product as an oil.

The NMR spectrum (CDCl$_3$) showed absorption at 1.4 (m, 3H), 2.4 (m, 2H), 4.2 (m, 1H), 4.52 (s, 1H), 4.60 (m, 2H), 4.63 (d, 1H, J=4 Hz), 5.22 (ABq, 2H, J=12 Hz) and 7.4 (s, 5H) ppm.

B. 6β-stearoyloxymethylpenicillanic acid sulfone

Following the procedure of Example 14B and starting with 776 mg. of benzyl 6β-stearoyloxymethylpenicillanate sulfone and 880 mg. of 5% palladium-on-calcium carbonate in 25 ml. of methanol-water (1:1) there was obtained 524 mg. of the calcium salt of the desired product. The calcium salt was subsequently suspended in 200 ml. of ethyl acetate and 200 ml. of water and treated with sufficient 6 N hydrochloric acid to give a pH of 2.0. The ethyl acetate layer was separated, backwashed with a brine solution and dried over magnesium sulfate. Removal of the solvent gave 260 mg. of the desired product as a white solid.

The NMR spectrum (CDCl$_3$ and DMSO-D$_6$) showed absorption at 1.4 (m, 3H), 2.35 (m, 2H), 4.2 (m, 1H), 4.39 (s, 1H), 4.60 (m, 2H) and 4.63 (d, 1H, J=4 Hz) ppm.

EXAMPLE 16

Starting with the appropriate acid chloride and requisite benzyl 6β-hydroxyalkylpenicillanate sulfone and employing the procedures in Example 14A and B, the following compounds are prepared:

6β-[1(R)acetoxy-n-butyl]penicillanic acid sulfone; 6β-[1(S)acetoxy-3-methyl-n-butyl]penicillanic acid sulfone; 6β-[1(S)acetoxy-2-phenethyl]penicillanic acid sulfone; 6β-[1(S)acetoxy-1-(3'-pyridyl)methyl]penicillanic acid sulfone; 6β-n-butyryloxymethylpenicillanic acid sulfone; 6β-[1(S)-s-butyryloxy-n-propyl]penicillanic acid sulfone; 6β-[1(S)-n-butyryloxy-2-methyl-n-propyl]penicillanic acid sulfone; 6β-[1(S)-n-butyryloxybenzyl]penicillanic acid sulfone; 6β-[1(R)-n-butyryloxy-1-(2'-pyridyl)methyl]penicillanic acid sulfone; 6β-[1(S)-s-butyryloxy-1-(4'-pyridyl)methyl]penicillanic acid sulfone; 6β-n-valeryloxymethylpenicillanic acid sulfone; 6β-[1(S)-n-valeryloxyethyl]penicillanic acid sulfone; 6β-[1(R)-i-valeryloxy-n-pentyl]penicillanic acid sulfone; 6β-[1(R)trimethylacetoxy-2,2-dimethyl-n-propyl]penicillanic acid sulfone; 6β-[1(R)-n-valeryloxy-3-phenylprophyl]penicillanic acid sulfone; 6β-[1(R)-i-valeryloxy-1-(2'-pyridyl)methyl]penicillanic acid sulfone; 6β-[1(S)-trimethylacetoxy-1-(4'-pyridyl)methyl]penicillanic acid sulfone; 6β-octanoyloxymethylpenicillanic acid sulfone; 6β-[1(R)octanoyloxy-n-pentyl]penicillanic acid sulfone; 6β-[1(S)octanoyloxy-2-phenethyl]penicillanic acid sulfone; 6β-[1(S)octanoyloxy-1-(3'-pyridyl)methyl]penicillanic acid sulfone; 6β-hendecanoyloxymethylpenicillanic acid sulfone; 6β-[1(S)hendecanoyloxy-2-methyl-n-propyl]penicillanic acid sulfone; 6β-[1(R)hendecanoyloxybenzyl]penicillanic acid sulfone; 6β-[1(S)hendecanoyloxy-1-(4'-pyridyl)methyl]penicillanic acid sulfone; 6β-palmitoyloxymethylpenicillanic acid sulfone; 6β-[1(S)palmitoyloxyethyl]penicillanic acid sulfone; 6β-[1(R)palmitoyloxy-2-phenethyl]penicillanic acid sulfone; 6β-[1(S)palmitoyloxy-1-(3'-pyridyl)methyl]penicillanic acid sulfone; 6β-[1(S)palmitoyloxy-1-(4'-pyridyl)methyl]penicillanic acid sulfone; 6β-[1(R)stearoyloxyethyl]penicillanic acid sulfone; 6β-[1(S)stearoyloxy-2,2-dimethyl-n-propyl]penicillanic acid sulfone; 6β-[1(R)stearoyloxy-3-phenylpropyl]penicillanic acid sulfone; 6β-[1(S)stearoyloxy-1-(2'-pyridyl)methyl]penicillanic acid sulfone; and 6β-[1(S)stearoyl-1-(4'-pyridyl)methyl]penicillanic acid sulfone.

EXAMPLE 17

6β-Benzoyloxymethylpenicillanic Acid Sulfone

A. benzyl benzoyloxymethylpenicillanic acid sulfone

To a solution of 300 mg. of benzyl 6β-hydroxymethylpenicillanate sulfone and 0.11 ml. of triethylamine in 25 ml. of methylene chloride cooled to 0°–5° C. was added 0.094 ml. of benzoyl chloride and 10 mg. of 4-dimethylaminopyridine. After stirring in the cold for 30 min. the solution was washed successively with water, water at pH 1.0, a saturated sodium bicarbonate solution and a brine solution. The organic phase was dried over magnesium sulfate and the solvent removed in vacuo. The residue was chromatographed on 20 g. of silica gel using toluene-ethyl acetate (8:1) as the eluent. Fractions 15 thru 30 were combined and concentrated in vacuo to give 280 mg. of the product as an oil.

The NMR spectrum (CDCl$_3$) showed absorption at 1.26 (s, 3H), 1.53 (s, 3H), 4.2 (m, 1H), 4.57 (s, 1H), 4.79

(d, 1H, J=4 Hz), 4.9 (m, 2H), 5.2 (ABq, 2H, J=12 Hz), 7.4 (s, 5H), 7.5 (m, 3H) and 8.2 (m, 2H) ppm.

B. 6β-benzoyloxymethylpenicillanic acid sulfone

To a suspension of 270 mg. of prereduced 5% palladium-on-calcium carbonate in 15 ml. of water-methanol (1:1) was added 270 mg. of benzyl 6β-benzoyloxymethylpenicillanic acid sulfone, and the resulting mixture was shaken in a hydrogen atmosphere at an initial pressure of 50 psi for 40 min. The catalyst was filtered and the methanol was evaporated. The residual aqueous was extracted with ethyl acetate and was then freeze dried to give the calcium salt of the product, 200 mg.

The NMR spectrum (D$_2$O) of the calcium salts showed absorption at 1.5 (s, 3H), 1.6 (s, 3H), 4.8 (m, 3H), 5.1 (d, 1H, J=4 Hz), 7.6 (m, 3H) and 8.0 (m, 2H) ppm.

EXAMPLE 18

Starting with the appropriate benzyl 6β-hydroxyalkylpenicillanate sulfone and requisite benzoyl chloride, and employing the procedures of Example 17A and B, the following esters are prepared:

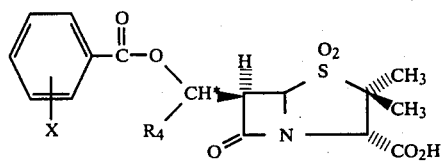

| X | R$_4$ | * |
|---|---|---|
| 4-Cl— | H— | — |
| 2-F— | H— | — |
| 4-CH$_3$— | H— | — |
| 4-Cl— | CH$_3$— | (S) |
| 4-Cl— | CH$_3$— | (R) |
| 4-CF$_3$— | CH$_3$— | (R) |
| 4-F— | CH$_3$(CH$_2$)$_2$— | (R) |
| 2-CH$_3$— | CH$_3$(CH$_2$)$_2$— | (R) |
| 3-CH$_3$O— | CH$_3$(CH$_2$)$_2$— | (R) |
| 2-F— | CH$_3$CH(CH$_3$)CH$_2$— | (S) |
| H— | CH$_3$(CH$_2$)$_2$— | (R) |
| H— | (CH$_3$)$_3$C— | (S) |
| 3-Cl— | (CH$_3$)$_3$C— | (R) |
| H— | C$_6$H$_5$— | (S) |
| 3-CH$_3$— | C$_6$H$_5$— | (S) |
| 4-CH$_3$O— | C$_6$H$_5$— | (R) |
| 2-F— | C$_6$H$_5$CH$_2$— | (S) |
| 2-CH$_3$— | C$_6$H$_5$(CH$_2$)$_2$— | (R) |
| 4-F— | C$_6$H$_5$(CH$_2$)$_2$— | (R) |
| 4-CF$_3$— | C$_6$H$_5$(CH$_2$)$_2$— | (S) |
| 4-CH$_3$— | C$_6$H$_5$(CH$_2$)$_2$— | (S) |
| H— | 2'-C$_5$H$_4$N— | (R) |
| 3-CH$_3$— | 2'-C$_5$H$_4$N— | (S) |
| 4-CF$_3$— | 2'-C$_5$H$_4$N— | (R) |
| H— | 3'-C$_5$H$_4$N— | (S) |
| 4-CH$_3$O— | 3'-C$_5$H$_4$N— | (S) |
| 4-CH$_3$— | 3'-C$_5$H$_4$N— | (S) |
| 3-F— | 3'-C$_5$H$_4$N— | (R) |
| H— | 4'-C$_5$H$_4$N— | (R) |
| 2-F— | 4'-C$_5$H$_4$N— | (R) |
| 4-CF$_3$— | 4'-C$_5$H$_4$N— | (S) |
| 4-CH$_3$— | 4'-C$_5$H$_4$N— | (S) |

EXAMPLE 19

6β-4'-Aminobenzoyloxymethylpenicillanic Acid Sulfone

A. benzyl 6β-4'-nitrobenzoyloxymethylpenicillanate sulfone

Under an argon atmosphere 264 mg. of 4'-nitrobenzoyl chloride and 10 mg. of 4-dimethylaminopyridine was added to 500 mg. of benzyl 6β-hydroxymethylpenicillanate sulfone and 0.196 ml. of triethylamine in 20 ml. of methylene chloride cooled to 0°–5° C. After stirring in the cold for 30 min. the reaction mixture was washed successively with water, water at pH 1.0, a saturated sodium bicarbonate solution and a brine solution. The organic phase was dried over magnesium sulfate and the solvent removed in vacuo to give 657 mg. of the product as a semi-solid.

The NMR spectrum (CDCl$_3$) showed absorption at 1.33 (s, 3H), 1.58 (s, 3H), 4.3 (m, 1H), 4.58 (s, 1H), 4.8 (d, 1H, J=4 Hz), 4.9 (m, 2H), 5.23 (ABq, 2H, J=12 Hz), 7.39 (s, 5H) and 8.2 (s, 4H) ppm.

B. 6β-4'-aminobenzoyloxymethylpenicillanic acid sulfone

To a suspension of 650 mg. of prereduced 5% palladium-on-calcium carbonate in 20 ml. of water-methanol (1:1) and 10 ml. of tetrahydrofuran was added 650 mg. of benzyl 6β-4'-nitrobenzoyloxymethylpenicillanic acid sulfone, and the resulting mixture was shaken in a hydrogen atmosphere at an initial pressure of 50 psi for one hour. The spent catalyst was filtered and the residue partitioned between ethyl acetate and water. The aqueous layer was separated and freeze dried to give 560 mg. of the product as the calcium salt.

The NMR spectrum (D$_2$O) of the calcium salt showed absorption at 1.5 (s, 3H), 1.6 (s, 3H), 4.39 (s, 1H), 4.70 (m, 3H), 5.1 (d, 1H, J=4 Hz), 6.78 (d, 2H, J=9 Hz) and 7.8 (d, 2H, J=9 Hz) ppm.

EXAMPLE 20

The procedures of Example 19 are repeated, starting with the requisite benzyl 6β-hydroxyalkylpenicillanate sulfone and appropriate nitrobenzoyl chloride, to give the following compounds as their calcium salts:

| NH$_2$ Ring Position | R$_4$ | * |
|---|---|---|
| 3- | H | — |
| 2- | H | — |
| 2- | CH$_3$— | (R) |
| 4- | CH$_3$— | (R) |
| 4- | CH$_3$— | (S) |
| 2- | CH$_3$(CH$_2$)$_2$— | (R) |
| 3- | CH$_3$(CH$_2$)$_2$— | (R) |
| 3- | CH$_3$CH(CH$_3$)CH$_2$— | (S) |
| 4- | CH$_3$CH(CH$_3$)CH$_2$— | (S) |
| 2- | (CH$_3$)$_3$C— | (R) |
| 3- | (CH$_3$)$_3$C— | (S) |
| 3- | C$_6$H$_5$— | (R) |
| 4- | C$_6$H$_5$— | (R) |
| 2- | C$_6$H$_5$CH$_2$— | (S) |
| 3- | C$_6$H$_5$CH$_2$— | (S) |
| 4- | C$_6$H$_5$CH$_2$— | (S) |
| 2- | C$_6$H$_5$(CH$_2$)$_2$— | (R) |
| 4- | C$_6$H$_5$(CH$_2$)$_2$— | (R) |
| 2- | 2-C$_5$H$_4$N— | (R) |
| 4- | 2-C$_5$H$_4$N— | (R) |
| 3- | 3-C$_5$H$_4$N— | (S) |
| 3- | 4-C$_5$H$_4$N— | (S) |
| 4- | 4-C$_5$H$_4$N— | (R) |

EXAMPLE 21

6β-4′-Tolylsulfonyloxymethylpenicillanic Acid Sulfone

A. benzyl 6β-4′-tolylsulfonyloxymethylpenicillanate

To 1.24 g. of 4-tolylsulfonylchloride in 3.5 ml. of pyridine cooled to 0° C. and under an argon atmosphere, 800 mg. of benzyl 6β-hydroxymethylpenicillanate in 1.5 ml. of pyridine was added dropwise. After stirring in the cold for 2 hrs., 0.80 ml. of water was added and the stirring continued for 30 min. at 0° C. The reaction mixture was added to 30 ml. of water and the pH adjusted to 1.0 with dilute hydrochloric acid. The aqueous was extracted with diethyl ether and the organic phase was separated and washed successively with 1.2 N hydrochloric acid, water and a brine solution. The organic layer was dried over magnesium sulfate and evaporated to an oil, 841 mg., which was chromatographed on 100 g. of silica gel using chloroform-ethyl acetate (10:1) as the eluent.

Fractions 10 thru 25 were combined and the solvent removed in vacuo to give 680 mg. of the product.

B. 6β-4′-tolylsulfonyloxymethylpenicillanic acid

To a suspension of 680 mg. of prereduced 5% palladium-on-calcium carbonate in 20 ml. of methanol-water (1:1) was added 680 mg. of benzyl 6β-4′-tolylsulfonyloxymethylpenicillanate, and the reduction continued at 49 psi for 30 min. An additional 680 mg. of catalyst was added and the reaction continued for an additional 30 min. The catalyst was filtered and the methanol evaporated from the filtrate. The aqueous residue was extracted with ethyl acetate and the aqueous layer acidified to pH 2.0. Fresh ethyl acetate was used to extract the acidified aqueous. The organic phase was separated dried over magnesium sulfate and the solvent removed in vacuo to give 463 mg. of the product as a semi-solid.

The NMR spectrum (CDCl$_3$) showed absorption at 1.57 (s, 3H), 1.6 (s, 3H), 2.37 (s, 3H), 4.1 (m, 3H), 4.2 (s, 1H), 5.4 (d, 1H, J=4 Hz), and 7.6 (ABq, 4H, J=10 Hz) ppm.

C. 6β-4′-tolylsulfonyloxymethylpenicillanic acid sulfone

Water (20 ml.) was added to a solution of 460 mg. of 6β-4′-tolylsulfonyloxymethylpenicillanic acid in 20 ml. of methylene chloride and the pH of the resulting mixture adjusted with a sodium hydroxide solution to 6.9. The aqueous layer was separated and the organic layer further extracted with water (2×20 ml.). To the combined water layer and washings was added dropwise 238 mg. of potassium permanganate in 5 ml. of water containing 0.16 ml. of phosphoric acid. During the reaction period (45 min.) the pH of the reaction was maintained at 6.0-6.4 by the addition of aqueous sodium hydroxide. The pH of the reaction mixture was then adjusted to 1.5 with 6 N hydrochloric acid and 20 ml. of ethyl acetate was added. After cooling the mixture to 0° C., 460 mg. of sodium bisulfite was added in one portion. The pH was readjusted to 1.5 with 6 N hydrochloric acid and the organic phase was separated, backwashed with a brine solution and dried over magnesium sulfate. Removal of the solvent gave 300 mg. of the product as a foam.

The NMR spectrum (CDCl$_3$) showed absorption at 1.45 (s, 3H), 1.65 (s, 3H), 2.45 (s, 3H), 4.4 (m, 3H), 4.42 (s, 1H), 4.8 (d, 1H, J=4 Hz) and 7.6 (ABq, 4H, J=10 Hz) ppm.

EXAMPLE 22

Starting with the appropriate sulfonyl chloride and requisite benzyl 6β-hydroxyalkylpenicillanate, and employing the procedures of Example 21, the following compounds are prepared:

| R$_3$ | R$_4$ | * |
|---|---|---|
| CH$_3$SO$_2$— | H— | — |
| (CH$_3$)$_2$CHSO$_2$— | H— | — |
| CH$_3$(CH$_2$)$_3$SO$_2$— | H— | — |
| CH$_3$SO$_2$— | CH$_3$— | (S) |
| CH$_3$SO$_2$— | (CH$_3$)$_2$CHCH$_2$— | (S) |
| CH$_3$CH$_2$SO$_2$— | C$_6$H$_5$— | (R) |
| CH$_3$SO$_2$— | 2′-C$_5$H$_4$N— | (S) |
| CH$_3$(CH$_2$)$_2$SO$_2$— | 4′-C$_5$H$_4$N— | (S) |
| C$_6$H$_5$SO$_2$— | C$_6$H$_5$(CH$_2$)$_2$— | (S) |
| C$_6$H$_5$SO$_2$— | CH$_3$(CH$_2$)$_2$— | (R) |
| C$_6$H$_5$SO$_2$— | H— | — |
| 2-CH$_3$C$_6$H$_4$SO$_2$— | H— | — |
| 4-CH$_3$C$_6$H$_4$SO$_2$— | CH$_3$— | (R) |
| 2-CH$_3$C$_6$H$_4$SO$_2$— | CH$_3$(CH$_2$)$_3$— | (R) |
| 3-CH$_3$C$_6$H$_4$SO$_2$— | C$_6$H$_5$(CH$_2$)$_2$— | (S) |
| 4-CH$_3$C$_6$H$_4$SO$_2$— | 3′-C$_5$H$_4$N— | (S) |
| 4-CH$_3$OC$_6$H$_4$SO$_2$— | H— | — |
| 4-CH$_3$OC$_6$H$_4$SO$_2$— | (CH$_3$)$_2$CH— | (S) |
| 3-CH$_3$OC$_6$H$_4$SO$_2$— | C$_6$H$_5$— | (S) |
| 2-CH$_3$OC$_6$H$_4$SO$_2$— | C$_2$H$_5$— | (R) |
| 4-CH$_3$OC$_6$H$_4$SO$_2$— | 4′-C$_5$H$_4$N— | (S) |
| 2-FC$_6$H$_4$SO$_2$— | H— | — |
| 4-FC$_6$H$_4$SO$_2$— | CH$_3$— | (S) |
| 3-FC$_6$H$_4$SO$_2$— | (CH$_3$)$_3$C— | (R) |
| 4-FC$_6$H$_4$SO$_2$— | C$_6$H$_5$CH$_2$— | (S) |
| 2-FC$_6$H$_4$SO$_2$— | 2′-C$_5$H$_4$N— | (S) |
| 2-ClC$_6$H$_4$SO$_2$— | H— | — |
| 2-ClC$_6$H$_4$SO$_2$— | (CH$_3$)$_2$CHCH$_2$— | (S) |
| 4-ClC$_6$H$_4$SO$_2$— | C$_6$H$_5$CH$_2$— | (R) |
| 4-ClC$_6$H$_4$SO$_2$— | C$_6$H$_5$(CH$_2$)$_2$— | (R) |
| 4-ClC$_6$H$_4$SO$_2$— | 4′-C$_5$H$_4$N— | (S) |
| 2-BrC$_6$H$_4$SO$_2$— | H— | — |
| 4-BrC$_6$H$_4$SO$_2$— | CH$_3$— | (R) |
| 4-BrC$_6$H$_4$SO$_2$— | C$_6$H$_5$— | (S) |
| 3-CF$_3$C$_6$H$_4$SO$_2$— | H— | — |
| 3-CF$_3$C$_6$H$_4$SO$_2$— | C$_2$H$_5$— | (R) |
| 4-CF$_3$C$_6$H$_4$SO$_2$— | H— | — |
| 4-CF$_3$C$_6$H$_4$SO$_2$— | CH$_3$— | (S) |
| 4-CF$_3$C$_6$H$_4$SO$_2$— | C$_6$H$_5$CH$_2$— | (S) |
| 4-CF$_3$C$_6$H$_4$SO$_2$— | 4′-C$_5$H$_4$N— | (R) |

EXAMPLE 23

6β-Sulfooxymethylpenicillanic Acid Sulfone

A. benzyl 6β-sulfooxymethylpenicillanate sulfone pyridinium salt

To a solution of 953 mg. of benzyl 6β-hydroxymethylpenicillanate sulfone in 75 ml. of dimethylacetamide under a nitrogen atmosphere is added 860 mg. of sulfur trioxide-pyridine complex and the reaction mixture allowed to stir for 45 min. at room temperature. The mixture is stirred into 400 ml. of hexane and allowed to stir for 30 min. The hexane is decanted and fresh hexane added. This procedure is repeated twice to give 900 mg. of the desired product.

B. 6β-sulfooxymethylpenicillanic acid sulfone

A mixture of 532 mg. of benzyl 6β-sulfooxymethylpenicillanate sulfone pyridinium salt in 10 ml. of water containing 174 mg. of sodium bicarbonate is added to a suspension of 500 mg. of prereduced 10% palladium-on-charcoal in 25 ml. of water, and the resulting mixture is shaken in a hydrogen atmosphere at 50 psi for one hour. An additional 500 mg. of catalyst is added and the reaction continued for 30 min. A final 500 mg. of catalyst is made and the reduction continued for 30 min. The catalyst is filtered and washed with water. The filtrate and washing are combined and freeze dried to give the crude product, which is purified by chromatographing on sephedex using water as the eluent. The fractions containing the product are combined and freeze dried to give the purified product.

EXAMPLE 24

Starting with the appropriate benzyl 6β-hydroxyalkylpenicillanate sulfone and employing the procedures of Example 23A and B, the following compounds, as their disodium salts are prepared:

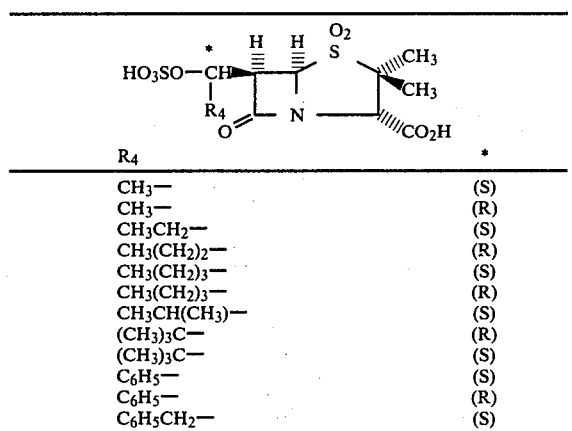

| | |
|---|---|
| $CH_3-$ | (S) |
| $CH_3-$ | (R) |
| $CH_3CH_2-$ | (S) |
| $CH_3(CH_2)_2-$ | (R) |
| $CH_3(CH_2)_3-$ | (S) |
| $CH_3(CH_2)_3-$ | (R) |
| $CH_3CH(CH_3)-$ | (S) |
| $(CH_3)_3C-$ | (R) |
| $(CH_3)_3C-$ | (S) |
| $C_6H_5-$ | (S) |
| $C_6H_5-$ | (R) |
| $C_6H_5CH_2-$ | (S) |

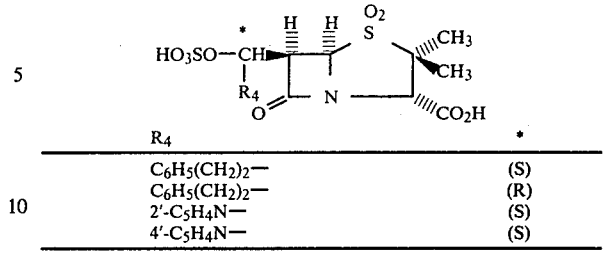

| | |
|---|---|
| $C_6H_5(CH_2)_2-$ | (S) |
| $C_6H_5(CH_2)_2-$ | (R) |
| $2'-C_5H_4N-$ | (S) |
| $4'-C_5H_4N-$ | (S) |

EXAMPLE 25

Pivaloyloxymethyl 6β-hydroxymethylpenicillanate sulfone

To a solution of 1.0 g. of 6β-hydroxymethylpenicillanic acid sulfone sodium salt in 10 ml. of dimethylformamide and cooled to 0°–5° C. was added 0.52 ml. of chloromethyl pivalate. After stirring overnight at room temperature, the reaction mixture was poured into a mixture of water-ethyl acetate. The ethyl acetate layer was separated, backwashed with water (3×100 ml.) and a brine solution (3×50 ml.) and dried over magnesium sulfate. The solvent was removed in vacuo to give 1.1 g. of the product as an oil.

The NMR spectrum (CDCl$_3$) showed absorption at 1.27 (s, 9H), 1.42 (s, 3H), 1.6 (s, 3H), 2.9 (bs, 1H), 4.2 (m, 3H), 4.58 (s, 1H), 4.75 (m, 1H) and 5.82 (ABq, 2H, $\delta_A-\delta_B=16$ Hz) ppm.

EXAMPLE 26

Employing the procedure of Example 25, and starting with the appropriate 6β-hydroxyalkylpenicillanic acid sulfone or derivative thereof and the requisite halide, the following esters are prepared:

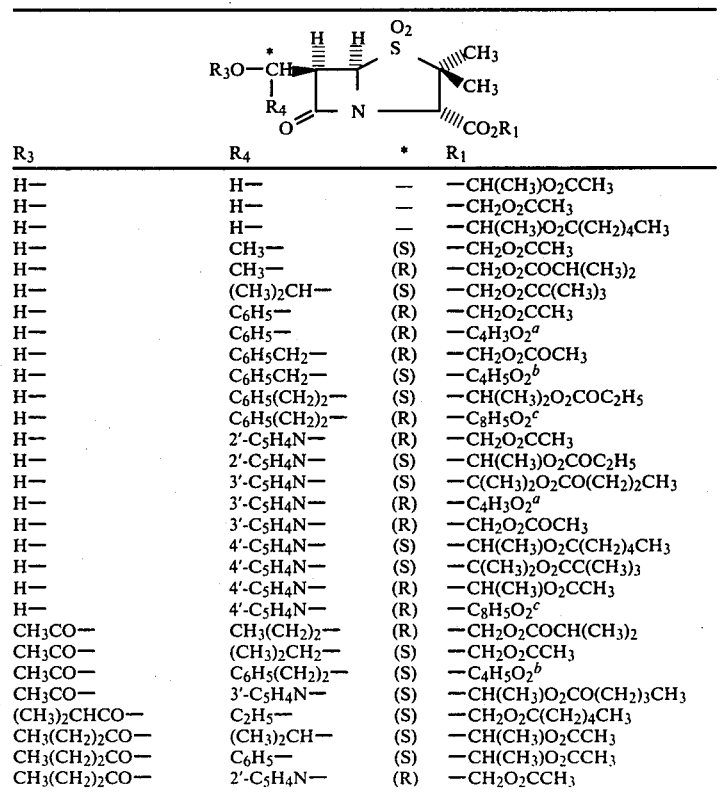

| $R_3$ | $R_4$ | * | $R_1$ |
|---|---|---|---|
| H— | H— | — | $-CH(CH_3)O_2CCH_3$ |
| H— | H— | — | $-CH_2O_2CCH_3$ |
| H— | H— | — | $-CH(CH_3)O_2C(CH_2)_4CH_3$ |
| H— | $CH_3-$ | (S) | $-CH_2O_2CCH_3$ |
| H— | $CH_3-$ | (R) | $-CH_2O_2COCH(CH_3)_2$ |
| H— | $(CH_3)_2CH-$ | (S) | $-CH_2O_2CC(CH_3)_3$ |
| H— | $C_6H_5-$ | (R) | $-CH_2O_2CCH_3$ |
| H— | $C_6H_5-$ | (R) | $-C_4H_3O_2{}^a$ |
| H— | $C_6H_5CH_2-$ | (R) | $-CH_2O_2COCH_3$ |
| H— | $C_6H_5CH_2-$ | (S) | $-C_4H_5O_2{}^b$ |
| H— | $C_6H_5(CH_2)_2-$ | (S) | $-CH(CH_3)_2O_2COC_2H_5$ |
| H— | $C_6H_5(CH_2)_2-$ | (R) | $-C_8H_5O_2{}^c$ |
| H— | $2'-C_5H_4N-$ | (R) | $-CH_2O_2CCH_3$ |
| H— | $2'-C_5H_4N-$ | (S) | $-CH(CH_3)O_2COC_2H_5$ |
| H— | $3'-C_5H_4N-$ | (S) | $-C(CH_3)_3O_2CO(CH_2)_2CH_3$ |
| H— | $3'-C_5H_4N-$ | (R) | $-C_4H_3O_2{}^a$ |
| H— | $3'-C_5H_4N-$ | (R) | $-CH_2O_2COCH_3$ |
| H— | $4'-C_5H_4N-$ | (S) | $-CH(CH_3)O_2C(CH_2)_4CH_3$ |
| H— | $4'-C_5H_4N-$ | (S) | $-C(CH_3)_3O_2CC(CH_3)_3$ |
| H— | $4'-C_5H_4N-$ | (R) | $-CH(CH_3)O_2CCH_3$ |
| H— | $4'-C_5H_4N-$ | (R) | $-C_8H_5O_2{}^c$ |
| $CH_3CO-$ | $CH_3(CH_2)_2-$ | (R) | $-CH_2O_2COCH(CH_3)_2$ |
| $CH_3CO-$ | $(CH_3)_2CH_2-$ | (S) | $-CH_2O_2CCH_3$ |
| $CH_3CO-$ | $C_6H_5(CH_2)_2-$ | (S) | $-C_4H_5O_2{}^b$ |
| $CH_3CO-$ | $3'-C_5H_4N-$ | (S) | $-CH(CH_3)O_2CO(CH_2)_3CH_3$ |
| $(CH_3)_2CHCO-$ | $C_2H_5-$ | (S) | $-CH_2O_2C(CH_2)_4CH_3$ |
| $CH_3(CH_2)_2CO-$ | $(CH_3)_2CH-$ | (S) | $-CH(CH_3)O_2CCH_3$ |
| $CH_3(CH_2)_2CO-$ | $C_6H_5-$ | (S) | $-CH(CH_3)O_2CCH_3$ |
| $CH_3(CH_2)_2CO-$ | $2'-C_5H_4N-$ | (R) | $-CH_2O_2CCH_3$ |

-continued

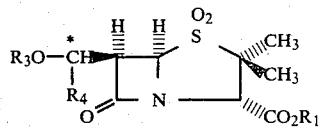

| R₃ | R₄ | * | R₁ |
|---|---|---|---|
| CH₃(CH₂)₂CO— | 4'-C₅H₄N— | (S) | —CH₂O₂CCH(CH₃)₂ |
| CH₃(CH₂)₃CO— | H— | — | —CH₂O₂CCH₃ |
| CH₃(CH₂)₃CO— | H— | — | —CH(CH₃)O₂CO(CH₂)₂CH₃ |
| (CH₃)₂CHCH₂CO— | CH₃(CH₂)₃— | (R) | —CH₂O₂CC(CH₃)₃ |
| (CH₃)₂CHCH₂CO— | 2'-C₅H₄N— | (R) | —C₄H₃O₂[a] |
| (CH₃)₃CCO— | 4'-C₅H₄N— | (S) | —CH(CH₃)O₂CCH₃ |
| CH₃(CH₂)₆CO— | H— | — | —C(CH₃)₂O₂CC(CH₃)₃ |
| CH₃(CH₂)₆CO— | C₆H₅CH₂— | (S) | —CH₂O₂CCH₃ |
| CH₃(CH₂)₆CO— | 3'-C₅H₄N— | (S) | —C₈H₅O₂[c] |
| CH₃(CH₂)₉CO— | H— | — | —CH(CH₃)O₂CCH₃ |
| CH₃(CH₂)₉CO— | H— | — | —CH(CH₃)O₂COC₂H₅ |
| CH₃(CH₂)₉CO— | (CH₃)₂CH— | (S) | —CH₂O₂COCH(CH₃)₂ |
| CH₃(CH₂)₁₄CO— | H— | — | —CH₂O₂CCH₃ |
| CH₃(CH₂)₁₄CO— | H— | — | —CH₂O₂C(CH₂)₄CH₃ |
| CH₃(CH₂)₁₄CO— | CH₃— | (S) | —CH(CH₃)O₂COCH₃ |
| CH₃(CH₂)₁₄CO— | CH₃— | (S) | —C₄H₅O₂[b] |
| CH₃(CH₂)₁₄CO— | 3'-C₅H₄N— | (S) | —CH₂O₂COCH₃ |
| CH₃(CH₂)₁₆CO— | H— | — | —CH₂O₂CC(CH₃)₃ |
| CH₃(CH₂)₁₆CO— | H— | — | —CH(CH₃)O₂COC₂H₅ |

[a] 4-crotonolactonyl
[b] γ-butyrolacton-4-yl
[c] 3-phthalidyl

EXAMPLE 27

Acetoxymethyl 6β-[1(S)methylsulfonyloxy-2-phenethyl]penicillanate Sulfone

To a solution of 2.22 g. of 6β-[1(R)ethylsulfonyloxybenzyl]penicillanic acid sulfone sodium salt in 30 ml. of dimethylformamide and cooled to 5° C. is added 648 mg. of chloromethyl acetate. The reaction mixture is allowed to stir at room temperature overnight, and is then poured into water-ethyl acetate. The ethyl acetate layer is separated, backwashed with water and dried over magnesium sulfate. Removal of the solvent in vacuo gives the desired product.

EXAMPLE 28

The procedure of Example 27 is employed, starting with the appropriate 6β-sulfonyloxyalkylpenicillanic acid sulfone and halide, to give the following products:

| R₃ | R₄ | * | R₁ |
|---|---|---|---|
| CH₃SO₂— | H— | — | —CH₂O₂CCH₃ |
| CH₃SO₂— | CH₃— | (S) | —CH(CH₃)O₂COC₂H₅ |
| CH₃CH₂SO₂ | C₆H₅— | (R) | —CH₂O₂COCH₃ |
| (CH₃)₂CHSO₂— | H— | — | —C(CH₃)₂O₂CO(CH₂)₂CH₃ |
| CH₃(CH₂)₂SO₂— | 4'-C₅H₄N— | (S) | —CH₂O₂CC(CH₃)₃ |
| CH₃(CH₂)₃SO₂— | H— | — | —C(CH₃)₂O₂CC(CH₃)₃ |
| 2-CH₃C₆H₄SO₂— | H— | — | —C₄H₃O₂[a] |
| 4-CH₃C₆H₄SO₂— | CH₃— | (R) | —CH₂O₂CCH(CH₃)₂ |
| 2-CH₃OC₆H₄SO₂— | C₂H₅— | (R) | —CH(CH₃)O₂COCH₃ |
| 3-CH₃OC₆H₄SO₂— | C₆H₅— | (S) | —CH₂O₂CCH₃ |
| 4-CH₃OC₆H₄SO₂— | 4'-C₅H₄N— | (S) | —CH₂O₂CCH₃ |
| 2-FC₆H₄SO₂— | H— | — | —CH₂O₂CCH₃ |
| 4-FC₆H₄SO₂— | CH₃— | (S) | —CH₂O₂CC(CH₃)₃ |
| 2-ClC₆H₄SO₂— | (CH₃)₂CHCH₂— | (S) | —C(CH₃)₂O₂CO(CH₂)₂CH₃ |
| 4-ClC₆H₄SO₂— | C₆H₅CH₂— | (R) | —CH₂O₂CCH₃ |
| 4-ClC₆H₄SO₂— | C₆H₅(CH₂)₂— | (R) | —CH₂O₂COCH₃ |
| 2-BrC₆H₄SO₂— | H— | — | —C₄H₅O₂[b] |
| 4-BrC₆H₄SO₂— | CH₃— | (R) | —C₈H₅O₂[c] |
| 3-CF₃C₆H₄SO₂— | C₂H₅— | (R) | —C(CH₃)₂O₂CCH₃ |
| 4-CF₃C₆H₄SO₂ | CH₃— | (S) | —CH₂O₂CO(CH₂)₂CH₃ |
| 4-CF₃C₆H₄SO₂— | C₆H₅CH₂— | (S) | —CH₂O₂COCH(CH₃)₂ |
| C₆H₅SO₂— | CH₃(CH₂)₂— | (R) | —CH₂COCH(CH₃)₂ |
| C₆H₅SO₂— | H— | — | —CH₂O₂CC(CH₃)₃ |
| C₆H₅SO₂— | C₆H₅(CH₂)₂— | (S) | —CH(CH₃)O₂CCH₃ |
| NaSO₃— | H— | — | —CH₂O₂CCH₃ |
| NaSO₃— | CH₃(CH₂)₂— | (R) | —CH(CH₃)O₂COC₂H₅ |
| NaSO₃— | C₆H₅CH₂— | (S) | —CH₂O₂CC(CH₃)₃ |

-continued

| R3 | R4 | * | R1 |
|---|---|---|---|
| NaSO3— | 2'-C5H4N— | (S) | —CH2O2COC2H5 |

[a]4-crotonolactonyl
[b]γ-butyrolacton-4-yl
[c]3-phthalidyl

EXAMPLE 29

Pivaloyloxymethyl 6β-Benzoyloxymethylpenicillanate Sulfone

To a solution of 1.95 g. of 6β-benzoyloxymethylpenicillanate sulfone sodium salt in 25 ml. of dry dimethylformamide cooled to 0°–5° C. is added 900 mg. of chloromethyl pivalate and the mixture allowed to stir overnight at room temperature. The mixture is then poured into a mixture of ethyl acetate-water. The ethyl acetate layer is separated, backwashed with water and a brine solution and dried over magnesium sulfate. Removal of the solvent in vacuo gave the desired product.

EXAMPLE 30

Starting with the appropriate 6β-hydroxyalkylpenicillanic acid sulfone derivative as the sodium salt and the requisite alkyl halide, and employing the procedure of Example 29, the following compounds are prepared:

| X | R4 | * | R1 |
|---|---|---|---|
| 4-Cl— | H— | — | —CH2O2CCH3 |
| 4-Cl— | CH3— | (R) | —CH(CH3)O2CCH3 |
| 3-Cl— | (CH3)3C— | (R) | —CH2O2CC(CH3)3 |
| 2-F— | H— | — | —CH(CH3)O2COC2H5 |
| 4-F— | CH3(CH2)2— | (R) | —CH2O2CC(CH3)3 |
| 3-F— | 3'-C5H4N— | (R) | —C(CH3)2O2CCH3 |
| 3-Br— | (CH3)2CHCH2— | (S) | —C4H3O2[a] |
| 4-Br— | C6H5CH2— | (R) | —CH2O2COCH3 |
| 2-CH3— | CH3(CH2)2— | (R) | —CH(CH3)O2COC2H5 |
| 3-CH3— | C6H5— | (S) | —CH2O2C(CH2)4CH3 |
| 4-CH3— | H— | — | —C8H5O2[c] |
| 4-CH3— | C6H5(CH2)2— | (S) | —CH2O2C(CH2)4CH3 |
| 4-CH3— | 4'-C5H4N— | (S) | —C(CH3)2O2COCH3 |
| H— | 4'-C5H4N— | (S) | —CH2O2CCH3 |
| H— | CH3(CH2)2— | (R) | —CH(CH3)O2CCH3 |
| 4-CF3— | CH3— | (R) | —C4H5O2[b] |
| 4-CF3 | C6H5(CH2)2— | (S) | —CH2O2COC2H5 |
| 3-CH3O— | CH3(CH2)2— | (R) | —CH2O2CC(CH3)3 |
| 4-CH3O— | C6H5— | (R) | —CH(CH3)O2COC2H5 |
| 4-CH3O— | 3'-C5H4N— | (S) | —C(CH3)2O2C(CH2)2CH3 |

[a]4-crotonolactonyl
[b]γ-butyrolacton-4-yl
[c]3-phthalidyl

EXAMPLE 31

Pivaloyloxymethyl 6β-4'-aminobenzoyloxymethylpenicillanate sulfone

A. pivaloyloxymethyl 6β-4'-nitrobenzoyloxymethylpenicillanate sulfone

To a cold solution of (0°–5° C.) of 1.89 g. of pivaloyloxymethyl 6β-hydroxymethylpenicillanate sulfone, 0.695 ml. of triethylamine and 10 mg. of 4-dimethylaminopyridine in 60 ml. of methylene chloride under an atmosphere of argon is added 1.11 g. of 4'-nitrobenzoyl chloride. The resulting reaction mixture is allowed to stir at room temperature for 2 hrs. and is then extracted with cold water. The organic layer is separated and washed successively with water at pH 1.0, a saturated sodium bicarbonate solution and a brine solution. The organic layer is then dried over magnesium sulfate and concentrated to dryness in vacuo to give the desired intermediate.

B. pivaloyloxymethyl 6β-4'-aminobenzoyloxymethylpenicillanate sulfone

To a solution of 500 mg. of pivaloyloxymethyl 6β-4'-nitrobenzoyloxymethylpenicillanate sulfone in 35 ml. of dimethoxyethane is added 250 mg. of 5% palladium-on-charcoal and the resulting suspension shaken in a hydrogen atmosphere at an initial pressure of 30 psi. After 3 hrs. the spent catalyst is filtered and the filtrate concentrated in vacuo to give the desired product.

EXAMPLE 32

Starting with the appropriate nitrobenzoyl chloride and 6β-hydroxyalkylpenicillanic acid ester sulfone and employing the procedure of Example 31A and B, the following compounds are prepared:

| NH2 Ring Position | R4 | * | R1 |
|---|---|---|---|
| 2 | H— | — | —CH2O2CCH3 |
| 4 | H— | — | —CH2O2COCH3 |
| 2 | CH3— | (S) | —CH2O2CCH3 |
| 3 | (CH3)2CH— | (S) | —CH2O2CC(CH3)3 |
| 4 | C6H5— | (R) | —C4H3O2[a] |
| 4 | C6H5CH2— | (S) | —C4H5O2[b] |
| 4 | C6H5(CH2)2— | (S) | —CH(CH3)O2COC2H5 |
| 3 | C6H5(CH2)2— | (R) | —C8H5O2[c] |
| 2 | 2'-C5H4N— | (R) | —CH2O2CCH3 |
| 4 | 4'-C5H4N— | (S) | —CH(CH3)O2C(CH2)4CH3 |
| 3 | 3'-C5H4N | (R) | —CH2O2COCH3 |

[a]4-crotonolactonyl
[b]γ-butyrolacton-4-yl
[c]3-phthalidyl

EXAMPLE 33

6β-Methoxycarbonyloxymethylpenicillanic Acid Sulfone

A. benzyl 6β-methoxycarbonyloxymethylpenicillanate sulfone

To a solution of 500 mg. of benzyl 6β-hydroxymethylpenicillanate sulfone and 0.196 ml. of triethylamine in 20 ml. of methylene chloride cooled to 0° C. is added 0.1 ml. of methyl chloroformate and 10 mg. of 4-dimethylaminopyridine. After stirring for 20 min. the solvent is removed under reduced pressure and ethyl acetate is added to the residue. The resulting solids are filtered, and the filtrate washed successively with water, water at pH 1.0, a saturated sodium bicarbonate solution and a brine solution. The organic phase is dried over magnesium sulfate and the solvent removed in vacuo to give the desired intermediate.

B. 6β-methoxycarbonyloxymethylpenicillanic acid sulfone

To a suspension of 600 mg. of 5% palladium-on-calcium carbonate, prereduced in 20 ml. of water with hydrogen at 50 psi for 20 min. is added 600 mg. of benzyl 6β-methoxycarbonyloxymethylpenicillanate sulfone. The resulting mixture is shaken in a hydrogen atmosphere at an initial pressure of 50 psi for 45 min. The catalyst is filtered and washed with methanol-water. The filtrate is treated with 75 ml. of ethyl acetate and the pH adjusted to 1.5 with 6 N hydrochloric acid. The organic phase is separated, dried over magnesium sulfate and concentrated in vacuo to give the final product.

EXAMPLE 34

Starting with the requisite benzyl 6β-hydroxyalkylpenicillanate sulfone and alkyl chloroformate, and employing the procedures of Example 33A and B, the following compounds are prepared:

| $R_3$ | $R_4$ | * |
|---|---|---|
| $C_2H_5OCO-$ | $CH_3-$ | (S) |
| $CH_3OCO-$ | $CH_3-$ | (R) |
| $CH_3OCO-$ | $C_2H_5-$ | (R) |
| $CH_3(CH_2)_2OCO-$ | $CH_3(CH_2)_2-$ | (R) |
| $(CH_3)_2CHOCO-$ | $(CH_3)_2CH-$ | (S) |
| $CH_3OCO-$ | $CH_3(CH_2)_4-$ | (S) |

| $R_3$ | $R_4$ | * |
|---|---|---|
| $CH_3(CH_2)_2-$ | $(CH_3)_3C-$ | (R) |
| $CH_3OCO-$ | $C_6H_5-$ | (S) |
| $C_2H_5OCO-$ | $C_6H_5CH_2-$ | (S) |
| $(CH_3)_2CHOCO-$ | $C_6H_5CH_2-$ | (R) |
| $CH_3OCO-$ | $C_6H_5(CH_2)_2-$ | (S) |
| $CH_3OCO-$ | $2'-C_5H_4N-$ | (R) |
| $CH_3OCO-$ | $2'-C_5H_4N-$ | (S) |
| $C_2H_5OCO-$ | $3'-C_5H_4N-$ | (R) |
| $CH(CH_2)_2OCO-$ | $3'-C_5H_4N-$ | (S) |
| $C_2H_5OCO-$ | $4'-C_5H_4N-$ | (S) |
| $CH_3OCO-$ | $4'-C_5H_4N-$ | (R) |

EXAMPLE 35

Acetoxymethyl 6β-Methoxycarbonyloxymethylpenicillanate sulfone

To a solution of 1.6 g. of 6β-methoxycarbonyloxymethylpenicillanic acid sulfone in 20 ml. of dry dimethylformamide at 5° C. and under a nitrogen atmosphere is added 120 mg. of sodium hydride. After stirring for 10 min. 648 mg. of chloromethyl acetate is added and the reaction mixture allowed to stir overnight at room temperature. The reaction mixture is poured into a mixture of water-ethyl acetate and the organic phase is subsequently separated, backwashed with water and a brine solution and dried over magnesium sulfate. Removal of the solvent in vacuo gives the final product.

EXAMPLE 36

The procedure of Example 35 is employed, starting with the appropriate 6β-alkoxycarbonyloxyalkylpenicillanic acid sulfone and alkyl chloride, to give the following compounds:

| $R_3$ | $R_4$ | * | $R_1$ |
|---|---|---|---|
| $C_2H_5OCO-$ | $CH_3-$ | (S) | $-CH_2O_2CCH_3$ |
| $CH_3OCO-$ | $C_2H_5-$ | (R) | $-CH(CH_3)O_2CCH_3$ |
| $CH_3(CH_2)_2OCO-$ | $CH_3(CH_2)_2-$ | (R) | $-CH_2O_2COC_2H_5$ |
| $(CH_3)_2CHOCO-$ | $(CH_3)_2CH-$ | (S) | $-CH(CH_3)O_2CO(CH_2)_3CH_3$ |
| $CH_3OCO-$ | $CH_3(CH_2)_4-$ | (S) | $-C_4H_3O_2{}^a$ |
| $CH_3OCO-$ | $CH_3(CH_2)_4-$ | (S) | $-C(CH_3)_2O_2CO(CH_2)_2CH_3$ |
| $C_2H_5OCO-$ | $C_6H_5CH_2-$ | (S) | $-CH_2O_2OCH_3$ |
| $CH_3OCO-$ | $C_6H_5(CH_2)_2-$ | (S) | $-C_4H_5O_2{}^b$ |
| $CH_3OCO-$ | $2'-C_5H_4N-$ | (R) | $-C_8H_5O_2{}^c$ |
| $C_2H_5OCO-$ | $3'-C_5H_4N-$ | (R) | $-CH(CH_3)O_2CCH_3$ |
| $C_2H_5OCO-$ | $3'-C_5H_4N-$ | (R) | $-CH(CH_3)O_2COC_2H_5$ |
| $C_2H_5OCO-$ | $4'-C_5H_4N-$ | (S) | $-CH_2O_2CC(CH_3)_3$ |
| $CH_3OCO-$ | $4'-C_5H_4N-$ | (R) | $-CH(CH_3)O_2CCH_3$ |

[a] 4-crotonolactonyl
[b] γ-butyrolacton-4-yl
[c] 3-phthalidyl

EXAMPLE 37

6β-Methylsulfonyloxymethylpenicillanic Acid

A. benzyl 6β-methylsulfonyloxymethylpenicillanate

To a cooled (−10° C.) solution of 800 mg. of benzyl 6β-hydroxymethylpenicillanate and 0.55 ml. of triethylamino in 25 ml. of methylene chloride was added 194 mg. of methylsulfonyl chloride. After one hour of stirring the reaction mixture was washed successively with water, water at pH 1.0, a saturated sodium bicarbonate solution and a brine solution. The organic phase was dried over magnesium sulfate and evaporated to dryness to give 650 mg. of the desired product.

B. 6β-methylsulfonyloxymethylpencillanic acid

To a suspension of 300 mg. of 5% palladium-on-calcium carbonate, prereduced with hydrogen at 47 psi for 15 min., in 20 ml. of methanol-water (1:1) was added 300 mg. of benzyl 6β-methylsulfonyloxymethylpenicillanate, and the reduction continued for 30 min at 47 psi. An additional 300 mg. of catalyst was added and the reduction continued for an additional 30 min. The spent catalyst was filtered and the methanol removed in vacuo from the filtrate. The aqueous residue was extracted with ethyl acetate and the pH of the aqueous adjusted to 2 with 6 N hydrochloric acid. The acidified aqueous was extracted with fresh ethyl acetate and the organic layer separated and backwashed with a saturated brine solution. The organic layer was dried over magnesium sulfate and evaporated to give 269 mg. of the desired product as an oil.

The NMR spectrum (CDCl₃) showed absorption at 1.56 (s, 3H), 1.68 (s, 3H), 3.06 (s, 3H), 4.1 (m, 1H), 4.41 (s, 1H), 4.52 (m, 2H), 5.47 (d, 1H, J=4 Hz) and 8.3 (s, 1H) ppm.

EXAMPLE 38

Starting with the appropriate sulfonyl chloride and benzyl 6β-hydroxymethylpenicillanate and employing the procedure of Example 37, the following compounds are prepared:

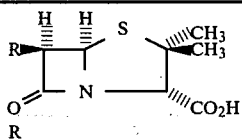

(CH₃)₂CHSO₂OCH₂—
CH₃(CH₂)₃SO₂OCH₂—
C₆H₅SO₂OCH₂—
2-CH₃C₆H₄SO₂OCH₂—
4-CH₃OC₆H₄SO₂OCH₂—
2-FC₆H₄SO₂OCH₂—
2-ClC₆H₄SO₂OCH₂—
2-BrC₆H₄SO₂OCH₂—
3-CF₃C₆H₄SO₂OCH₂—
4-CF₃C₆H₄SO₂OCH₂—

EXAMPLE 39

6β-[1-(S)Hydroxy-3-phenylpropyl]penicillanic Acid

To a suspension of 244 mg. of 5% palladium-on-calcium carbonate, prereduced with hydrogen at 50 psi for 20 min., in 20 ml. of methanol-water (1:1) was added 244 mg. of benzyl 6β-[1(S)hydroxy-3-phenylpropyl]penicillanate (Example 11B), and the resulting mixture shaken in a hydrogen atmosphere at an initial pressure of 52 psi for one hour. At this time an additional 244 mg. of catalyst was added and the hydrogenation continued for one hour. An additional 244 mg. of catalyst was again added and the reduction completed in one hour. The catalyst was filtered and the methanol removed in vacuo.

The aqueous residue was extracted with ethyl acetate and was then acidified to pH 1.8 with 6 N hydrochloric acid. The acidified aqueous was extracted with fresh ethyl acetate, and the organic phase separated, backwashed with a brine solution and dried over magnesium sulfate. Removal of the solvent under reduced pressure gave 127 mg. of the desired product, m.p. 135°–137.5° C.

The NMR spectrum (CDCl₃, DMSO-D₆) showed absorption at 1.57 (s, 3H), 1.59 (s, 3H), 1.8 (m, 2H), 2.8 (m, 2H), 3.6 (d, d, J=10, 4 Hz), 4.0 (m, 1H), 4.13 (s, 1H), 5.4 (d, 1H, J=4 Hz) and 7.2 (s, 5H) ppm.

EXAMPLE 40

6β-[1(R)Hydroxy-3-phenylpropyl]penicillanic Acid

To a suspension of 369 mg. of 5% palladium-on-calcium carbonate, prereduced with hydrogen at 52 psi for 20 min, in 20 ml. of methanol-water (1:1) was added 369 mg. of benzyl 6β-[1(R)hydroxy-3-phenylpropyl]penicillanate (Example 11B), and the resulting mixture shaken in a hydrogen atmosphere at 52 psi for one hour. Three 370 mg. portions of the catalyst were added every hour over a three hour period, followed by hydrogen at 52 psi. One hour after the last addition the catalyst was filtered and the methanol removed from the filtrate. The aqueous residue was extracted with ethyl acetate and then acidified to pH 1.5 with 6 N hydrochloric acid. Fresh ethyl acetate was added to the acidified aqueous and the organic phase separated, washed with a brine solution and dried over magnesium sulfate. Removal of the solvent in vacuo gave 110 mg. of the desired product, m.p. 131°–135° C.

The NMR spectrum (CDCl₃, DMSO-D₆) showed absorption at 1.53 (s, 3H), 1.65 (s, 3H), 1.8 (m, 2H), 2.8 (m, 2H), 3.5 (d, d, J=9 4 Hz), 4.1 (m, 1H), 4.3 (s, 1H), 5.3 (d, 1H, J—4 Hz) and 7.3 (s, 5H) ppm.

EXAMPLE 41

Pivaloyoxymethyl 6β-methylsulfonyloxymethylpenicillanate

To a solution of 1.0 g. of 6β-methylsulfonyloxymethylpenicillanic acid sodium salt in 10 ml. of dimethylformamide cooled to 0°–5° C. is added 0.53 ml. of chloromethyl pivalate, and the resulting reaction mixture allowed to stir at room temperature overnight. The mixture is poured into water-ethyl acetate, and the organic layer separated, backwashed with a brine solution and dried over magnesium sulfate. Removal of the solvent in vacuo gives the desired product.

EXAMPLE 42

Starting with the appropriate penicillanic acid and requisite halide, and employing the procedure of Example 41, the following compounds are prepared:

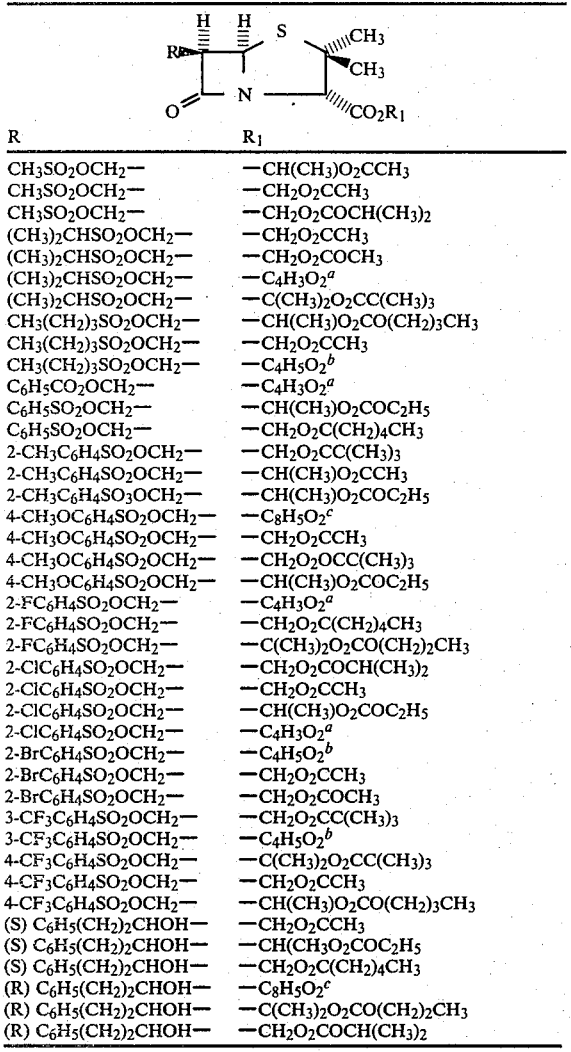

| R | R₁ |
|---|---|
| CH₃SO₂OCH₂— | —CH(CH₃)O₂CCH₃ |
| CH₃SO₂OCH₂— | —CH₂O₂CCH₃ |
| CH₃SO₂OCH₂— | —CH₂O₂COCH(CH₃)₂ |
| (CH₃)₂CHSO₂OCH₂— | —CH₂O₂CCH₃ |
| (CH₃)₂CHSO₂OCH₂— | —CH₂O₂COCH₃ |
| (CH₃)₂CHSO₂OCH₂— | —C₄H₃O₂ᵃ |
| (CH₃)₂CHSO₂OCH₂— | —C(CH₃)₂O₂CC(CH₃)₃ |
| CH₃(CH₂)₃SO₂OCH₂— | —CH(CH₃)O₂CO(CH₂)₃CH₃ |
| CH₃(CH₂)₃SO₂OCH₂— | —CH₂O₂CCH₃ |
| CH₃(CH₂)₃SO₂OCH₂— | —C₄H₃O₂ᵇ |
| C₆H₅CO₂OCH₂— | —C₄H₃O₂ᵃ |
| C₆H₅SO₂OCH₂— | —CH(CH₃)O₂COC₂H₅ |
| C₆H₅SO₂OCH₂— | —CH₂O₂C(CH₂)₄CH₃ |
| 2-CH₃C₆H₄SO₂OCH₂— | —CH₂O₂CC(CH₃)₃ |
| 2-CH₃C₆H₄SO₂OCH₂— | —CH(CH₃)O₂CCH₃ |
| 2-CH₃C₆H₄SO₃OCH₂— | —CH(CH₃)O₂COC₂H₅ |
| 4-CH₃OC₆H₄SO₂OCH₂— | —C₈H₅O₂ᶜ |
| 4-CH₃OC₆H₄SO₂OCH₂— | —CH₂O₂CCH₃ |
| 4-CH₃OC₆H₄SO₂OCH₂— | —CH₂O₂CC(CH₃)₃ |
| 4-CH₃OC₆H₄SO₂OCH₂— | —CH(CH₃)O₂COC₂H₅ |
| 2-FC₆H₄SO₂OCH₂— | —C₄H₃O₂ᵃ |
| 2-FC₆H₄SO₂OCH₂— | —CH₂O₂C(CH₂)₄CH₃ |
| 2-FC₆H₄SO₂OCH₂— | —C(CH₃)₂O₂CO(CH₂)₂CH₃ |
| 2-ClC₆H₄SO₂OCH₂— | —CH₂O₂COCH(CH₃)₂ |
| 2-ClC₆H₄SO₂OCH₂— | —CH₂O₂CCH₃ |
| 2-ClC₆H₄SO₂OCH₂— | —CH(CH₃)O₂COC₂H₅ |
| 2-ClC₆H₄SO₂OCH₂— | —C₄H₃O₂ᵃ |
| 2-BrC₆H₄SO₂OCH₂— | —C₄H₃O₂ᵇ |
| 2-BrC₆H₄SO₂OCH₂— | —CH₂O₂CCH₃ |
| 2-BrC₆H₄SO₂OCH₂— | —CH₂O₂COCH₃ |
| 3-CF₃C₆H₄SO₂OCH₂— | —CH₂O₂CC(CH₃)₃ |
| 3-CF₃C₆H₄SO₂OCH₂— | —C₄H₃O₂ᵇ |
| 4-CF₃C₆H₄SO₂OCH₂— | —C(CH₃)₂O₂CC(CH₃)₃ |
| 4-CF₃C₆H₄SO₂OCH₂— | —CH₂O₂CCH₃ |
| 4-CF₃C₆H₄SO₂OCH₂— | —CH(CH₃)O₂CO(CH₂)₃CH₃ |
| (S) C₆H₅(CH₂)₂CHOH— | —CH₂O₂CCH₃ |
| (S) C₆H₅(CH₂)₂CHOH— | —CH(CH₃O₂COC₂H₅ |
| (S) C₆H₅(CH₂)₂CHOH— | —CH₂O₂C(CH₂)₄CH₃ |
| (R) C₆H₅(CH₂)₂CHOH— | —C₈H₅O₂ᶜ |
| (R) C₆H₅(CH₂)₂CHOH— | —C(CH₃)₂O₂CO(CH₂)₂CH₃ |
| (R) C₆H₅(CH₂)₂CHOH— | —CH₂O₂COCH(CH₃)₂ |

I claim:

1. A compound selected from the formulae

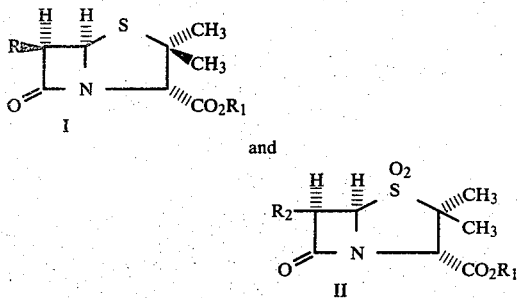

or pharmaceutically acceptable base salt thereof, wherein R is 1-hydroxy-3-phenylpropyl; $R_1$ is selected from the group consisting of benzyl, hydrogen and ester-forming residues readily hydrolyzable in vivo; $R_2$ is

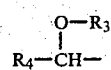

wherein $R_3$ is selected from the group consisting of sulfo, hydrogen, alkoxycarbonyl having from two to four carbon atoms, alkanoyl having from two to eighteen carbon atoms, benzoyl, substituted benzoyl wherein said substituent is selected from the group consisting of amino, methyl, methoxy, fluoro, chloro, bromo and trifluoromethyl, alkylsulfonyl having from one to four carbon atoms, phenylsulfonyl and substituted phenylsulfonyl wherein said substituent is selected from the group consisting of methyl, methoxy, fluoro, chloro, bromo and trifluoromethyl; and $R_4$ is selected from the group consisting of hydrogen, alkyl having one to four carbon atoms, phenyl, pyridyl, benzyl and β-phenethyl.

2. A compound of claim 1, Formula II, wherein $R_1$ is hydrogen.

3. A compound of claim 2, wherein $R_4$ is hydrogen.

4. The compound of claim 3, wherein $R_3$ is hydrogen.

5. The compound of claim 3, wherein $R_3$ is acetyl.

6. The compound of claim 3, wherein $R_3$ is stearoyl.

7. The compound of claim 3, wherein $R_3$ is benzoyl.

8. A compound of claim 2, wherein $R_3$ is hydrogen and $R_4$ is alkyl having from one to four carbon atoms.

9. The compound of claim 8, wherein $R_4$ is methyl.

10. A compound of claim 1, Formula I, wherein $R_1$ is hydrogen.

11. The compound of claim 10, wherein R is 1-hydroxy-3-phenylpropyl.

12. A pharmaceutical composition useful for treating bacterial infections in mammals, which comprises a pharmaceutically acceptable carrier, a β-lactam antibiotic and a compound selected from the formulae

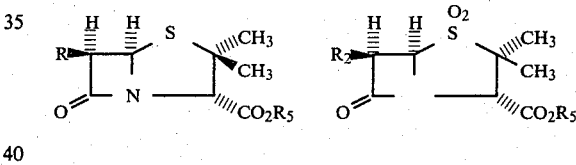

or a pharmaceutically acceptable base salt thereof, wherein R is selected from the group consisting of alkylsulfonyloxymethyl having from one to four carbon atoms in the alkyl group, phenylsulfonyloxymethyl, substituted phenylsulfonyloxymethyl wherein said substituent is selected from the group consisting of methyl, methoxy, fluoro, chloro, bromo and trifluoromethyl and 1-hydroxy-3-phenylpropyl; $R_2$ is

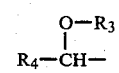

wherein $R_3$ is selected from the group consisting of sulfo, hydrogen, alkoxycarbonyl having from two to four carbon atoms, alkanoyl having from two to eighteen carbon atoms, benzoyl, substituted benzoyl wherein said substituent is selected from the group consisting of amino, methyl, methoxy, fluoro, chloro, bromo and trifluoromethyl, alkylsulfonyl having from one to four carbon atoms, phenylsulfonyl and substituted phenylsulfonyl wherein said substituent is selected from the group consisting of methyl, methoxy, fluoro, chloro, bromo and trifluoromethyl, and $R_4$ is selected from the group consisting of hydrogen, alkyl having one to four carbon atoms, phenyl, pyridyl, benzyl and β-phenethyl; R₅ is selected from the group consisting of hydrogen and ester-forming residues readily hydrolyzable in vivo.

13. A pharmaceutical composition of claim 12, wherein R₅ is selected from the group consisting of hydrogen and ester-forming residues readily hydrolyzable in vivo selected from the group consisting of alkanoyloxymethyl having from three to six carbon atoms, 1-(alkanoyloxy)ethyl having from four to seven carbon atoms, 1-methyl-1-(alkanoyloxy)ethyl having from five to eight carbon atoms, alkoxycarbonyloxymethyl having from three to six carbon atoms, 1-(alkoxycarbonyloxy)ethyl having from four to seven carbon atoms, 1-methyl-1-(alkoxycarbonyloxy)ethyl having from five to eight carbon atoms, 3-phthalidyl, 4-crotonolactonyl and γ-butyrolacton-4-yl.

14. A pharmaceutical composition of claim 13, wherein said β-lactam antibiotic is selected from the group consisting of:

6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)-penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-2-[3-methylsulfonylimidazolidin-2-one-1-carboxamido]-2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)penicillanic acid,
6-(2,2-dimethyl-5-oxo-4-phenyl-1-imidazolidinyl)penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-formyloxy-2-phenylacetamido)-3-(5-[1-methyltetrazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(D-2-amino-2-p-hydroxyphenylacetamido)desacetoxycephalosporanic acid,
7-(2-[4-pyridylthio]acetamido)cephalosporanic acid,
7-(D-2-amino-2[1,4-cyclohexadienyl]acetamido)cephalosporanic acid,
7-(D-2-amino-2-phenylacetamido)cephalosporanic acid,
7-[D-(-)-alpha-(4-ethyl-2,3-dioxo-1-piperazinecarboxamido)alpha-(4-hydroxyphenyl)acetamido]-3-[(1-methyl-1,2-3,4-tetrazol-5-yl)thiomethyl]-3-cephem-4-carboxylic acid,
7-(D-2-amino-2-phenylacetamido)-3-chloro-3-cephem-4-carboxylic acid,
7-[2-(2-amino-4-thiazolyl)-2-(methoximino)acetamido]cephalosporanic acid,
[6R,7R-3-carbamoyloxymethyl-7(2Z)-2-methoxyimino(fur-2-yl)acetamido-ceph-3-em-4-carboxylate]
7-[2-(2-aminothiazol-4-yl)acetamido]-3-[((1-2-dimethylaminoethyl)-1H-tetrazol-5-yl)thio)methyl]-ceph-3-em-4-carboxylic acid, and a pharmaceutically acceptable salts thereof.

15. A pharmaceutical composition of claim 14, Formula IV, wherein R₅ is hydrogen.

16. A pharmaceutical composition of claim 15, wherein R₃ and R₄ are each hydrogen.

17. A pharmaceutical composition of claim 15, wherein R₃ is acetyl and R₄ is hydrogen.

18. A pharmaceutical composition of claim 15, wherein R₃ is stearoyl and R₄ is hydrogen.

19. A pharmaceutical composition of claim 15, wherein R₃ is benzoyl and R₄ is hydrogen.

20. A pharmaceutical composition of claim 15, wherein R₃ is hydrogen and R₄ is methyl.

21. A pharmaceutical composition of claim 14, Formula III, wherein R₅ is hydrogen.

22. A pharmaceutical composition of claim 21, wherein R is methylsulfonyloxymethyl.

23. A pharmaceutical composition of claim 21, wherein R is p-toluenesulfonyloxymethyl.

24. A pharmaceutical composition of claim 21, wherein R is 1-hydroxy-3-phenylpropyl.

25. A method of increasing the effectiveness of a β-lactam antibiotic in a mammalian subject, which comprises co-administering to said subject a β-lactam antibiotic effectiveness increasing amount of a compound of the formulae

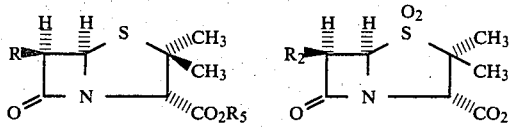

III and IV or a pharmaceutically acceptable base salt thereof, wherein R is selected from the group consisting of alkylsulfonyloxymethyl having from one to four carbon atoms in the alkyl group, phenylsulfonyloxymethyl, substituted phenylsulfonyloxymethyl wherein said substituent is selected from the group consisting of methyl, methoxy, fluoro, chloro, bromo and trifluoromethyl and 1-hydroxy-3-phenylpropyl; $R_2$ is

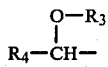

wherein $R_3$ is selected from the group consisting of sulfo, hydrogen, alkoxycarbonyl having from two to four carbon atoms, alkanoyl having from two to eighteen carbon atoms, benzoyl, substituted benzoyl wherein said substituent is selected from the group consisting of amino, methyl, methoxy, fluoro, chloro, bromo and trifluoromethyl, alkylsulfonyl having from one to four carbon atoms, phenylsulfonyl and substituted phenylsulfonyl wherein said substituent is selected from the group consisting of methyl, methoxy, fluoro, chloro, bromo and trifluoromethyl; and $R_4$ is selected from the group consisting of hydrogen, alkyl having one to four carbon atoms, phenyl, pyridyl, benzyl and β-phenethyl; $R_5$ is selected from the group consisting of hydrogen and ester-forming residues readily hydrolyzable in vivo.

26. The method of claim 25, wherein $R_5$ is selected from the group consisting of hydrogen and ester-forming residues readily hydrolyzable in vivo selected from the group consisting of alkanoyloxymethyl having from three to six carbon atoms, 1-(alkanoyloxy)ethyl having from four to seven carbon atoms, 1-methyl-1-(alkanoyloxy)ethyl having from five to eight carbon atoms, alkoxycarbonyloxymethyl having from three to six carbon atoms, 1-(alkoxycarbonyloxy)ethyl having from four to seven carbon atoms, 1-methyl-1-(alkoxycarbonyl)ethyl having from five to eight carbon atoms, 3-phthalidyl, 4-crotonolactonyl and γ-butyrolacton-4-yl.

27. The method of claim 26, wherein said β-lactam antibiotic is selected from the group consisting of:
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)-penicillanic acid,
6-(D-2-amino-2-[1,4-cyclohexadienyl]acetamido)-penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)-penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-2-[3-methylsulfonylimidazolidin-2-one-1-carboxamido]-2-phenylacetamido)penicillanic acid,
6-([hexahydro-1H-azepin-1-yl]methyleneamino)-penicillanic acid,
acetoxymethyl 6-(2-phenylacetamido)penicillanate,
acetoxymethyl 6-(D-2-amino-2-phenylacetamido)-penicillanate,
acetoxymethyl 6-(D-2-amino-2-[4-hydroxyphenyl]acetamido)-penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)-penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)-penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)-penicillanic acid,
6-(2-tolyloxycarbonyl-2-[3-thienyl]acetamido)-penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)-penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-formyloxy-2-phenylacetamido)-3-(5-[1-methyltetrazolyl]thiomethyl)-3-desacetoxymethylcephalosporanic acid,
7-(D-2-amino-2-phenylacetamido)desacetoxycephalosporanic acid, 7-alpha-methoxy-7-(2-[2-thienyl]acetamido)-3-carbamoyloxymethyl-3-desacetoxymethylcephalosporanic acid, 7-(2-cyanoacetamido)cephalosporanic acid, 7-(D-2-hydroxy-2-phenylacetamido)-3-(5-[1-methyltetrazolyl]thiomethyl)-3-desacetoxymethylcephalosporanic acid, 7-(D-2-amino-2-p-hydroxypehnylacetamido)-desacetoxycephalosporanic acid, 7-(2-[4-pyridylthio]acetamido)cephalosporanic acid, 7-(D-2-amino-2[1,4-cyclohexadienyl]acetamido)-cephalosporanic acid, 7-(D-2-amino-2-phenylacetamido)cephalosporanic acid, 7-[D-(-)-alpha-(4-ethyl-2,3-dioxo-1-piperazinecarboxamido)alpha-(4-hydroxyphenyl)acetamido]-3-[(1-methyl-1,2-3,4-tetrazol-5-yl)thiomethyl]-3-cephem-4-carboxylic acid, 7-(D-2-amino-2-phenylacetamido)-3-chloro-3-cephem-4-carboxylic acid, 7-[2-(2-amino-4-thiazolyl)-2-(methoximino)acetamido]cephalosporanic acid,

[6R,7R-3-carbamoyloxymethyl-7(2Z)-2-methoxyimino(fur-2-yl)acetamido-ceph-3-em-4-carboxylate]

7-[2-(2-aminothiazol-4-yl)acetamido]-3-[([1-2-dimethylaminoethyl)-1H-tetrazol-5-yl]thio)methyl]-ceph-3-em-4-carboxylic acid, and a pharmaceutically acceptable salts thereof.

28. The method of claim 27, Formula IV, wherein $R_5$ is hydrogen.

29. The method of claim 28, wherein $R_3$ and $R_4$ are each hydrogen.

30. The method of claim 28, wherein $R_3$ is acetyl and $R_4$ is hydrogen.

31. The method of claim 28, wherein $R_3$ is stearoyl and $R_4$ is hydrogen.

32. The method of claim 28, wherein $R_3$ is benzoyl and $R_4$ is hydrogen.

33. The method of claim 28, wherein $R_3$ is hydrogen and $R_4$ is methyl.

34. The method of claim 27, Formula III, wherein $R_5$ is hydrogen.

35. The method of claim 34, wherein R is methylsulfonyloxymethyl.

36. The method of claim 24, wherein R is p-toluenesulfonyloxymethyl.

37. The method of claim 34, wherein R is 1-hydroxy-3-phenylpropyl.

* * * * *